(12) United States Patent
Monoi et al.

(10) Patent No.: US 7,388,059 B2
(45) Date of Patent: Jun. 17, 2008

(54) ETHYLENE POLYMER, CATALYST FOR PRODUCING THEREOF AND METHOD FOR PRODUCING THEREOF

(75) Inventors: Takashi Monoi, Kawasaki (JP); Hidenobu Torigoe, Kawasaki (JP)

(73) Assignee: Japan Polyethylene Corporation, Tokyo (JP)

( * ) Notice: Subject to any disclaimer, the term of this patent is extended or adjusted under 35 U.S.C. 154(b) by 447 days.

(21) Appl. No.: 10/876,717

(22) Filed: Jun. 28, 2004

(65) Prior Publication Data
US 2005/0288459 A1   Dec. 29, 2005

(51) Int. Cl.
C08F 4/24 (2006.01)
C08F 110/02 (2006.01)

(52) U.S. Cl. .............. 526/106; 526/352; 526/65; 526/68; 526/69; 526/125.1; 526/348

(58) Field of Classification Search ........... 526/106, 526/65, 68, 69, 125.1, 348, 352
See application file for complete search history.

(56) References Cited

U.S. PATENT DOCUMENTS 6,252,017 B1 * 6/2001 Debras et al. ............ 526/65

FOREIGN PATENT DOCUMENTS

| GB | 1 501 728 | * | 2/1978 |
|----|-----------|---|--------|
| JP | 47-1365 | | 1/1972 |
| JP | 47-23176 | | 6/1972 |
| JP | 49-13230 | | 3/1974 |
| JP | 51-3360 | | 2/1976 |
| JP | 51-17993 | | 2/1976 |
| JP | 57-70109 | | 4/1982 |
| JP | 58-96606 | | 6/1983 |
| JP | 2-185506 | | 7/1990 |
| JP | 3-23564 | | 3/1991 |
| JP | 4-249502 | | 9/1992 |
| JP | 9-25312 | | 1/1997 |
| JP | 11-189602 | | 7/1999 |
| JP | 11-236415 | | 8/1999 |
| JP | 11-302465 | | 11/1999 |
| JP | 2000-86718 | | 3/2000 |
| JP | 2000-198811 | | 7/2000 |
| JP | 2001-294613 | * | 10/2001 |
| JP | 2002-80521 | | 3/2002 |
| WO | WO 94/13708 | * | 6/1994 |

OTHER PUBLICATIONS

M.P. McDaniel, "Supported Chromium Catalysts for Ethylene Polymerization", Advances in Catalysis, vol. 33, 1985, pp. 47-98.
C.E. Marsden, "The Influence of Silica Support on Polymerisation Catalyst Performance", Preparation of Catalysts, vol. 5, 1991, pp. 215-227.
C.E. Marsden, "Advances in Supported Chromium Catalysts", Plastics, Rubber and Composites Processing and Applications, vol. 21, 1994, pp. 193-200.
T. Mole, et al., "Organoaluminium Alkoxides and Related Compounds", Organoaluminium Compounds, 3rd Edition, Chapter 8, 1972, 15 Pages.

* cited by examiner

Primary Examiner—Ling-Siu Choi
(74) Attorney, Agent, or Firm—Oblon, Spivak, McClelland, Maier & Neustadt, P.C.

(57) ABSTRACT

A method for producing an ethylene polymer which comprises continuously polymerizing ethylene alone or copolymerizing ethylene and a $C_3$-$C_8$ α-olefin by multistage polymerization in a plurality of polymerization reactors connected in series in the presence of a chromium catalyst having at least a part of chromium atoms converted to hexavalent chromium carried on an inorganic oxide carrier by calcination-activating in a non-reducing atmosphere, wherein an organoaluminum compound of the formula (1):

$$(R^1)_x Al(OR^2)_y (OSiR^3 R^4 R^5)_z \qquad (1)$$

(in the above formula, $R^1$ and $R^2$ may be the same or different, each represents a $C_1$-$C_{18}$ alkyl group or a $C_6$-$C_{18}$ aryl group, $R^3$, $R^4$ and $R^5$ may be the same or different, each represents a $C_1$-$C_{18}$ alkyl group or a $C_6$-$C_{18}$ aryl group, $R^1$, $OR^2$ and $OSiR^3 R^4 R^5$ respectively may be the same or different when each has a plurality of kinds, and x, y and z are respectively $0 \leq x \leq 3$, $0 \leq y < 3$, $0 \leq z < 3$, and $x+y+z=3$) is introduced at least one or all of the polymerization reactors.

3 Claims, No Drawings

ETHYLENE POLYMER, CATALYST FOR PRODUCING THEREOF AND METHOD FOR PRODUCING THEREOF

FIELD OF THE INVENTION

The present invention relates to a method for producing an ethylene polymer by using a chromium catalyst and a specific organoaluminum compound. Particularly, the present invention relates to a method for producing an ethylene polymer by multistage polymerization using a chromium catalyst and a specific organoaluminum compound, an ethylene polymer obtained by this method and a molded product using this polymer. The ethylene polymer obtained by the method of the present invention is excellent in environmental stress cracking resistance (hereinafter referred to as "ESCR") and creep resistance, and particularly has excellent properties as a blow molded product and an extrusion molded product.

PRIOR ARTS

An ethylene polymer obtained by using a chromium catalyst supported on an inorganic oxide support, at least a part of chromium atoms of which is converted to hexavalent state by calcination-activating in a non-reducing atmosphere (so-called "Phillips catalyst") has a relatively wide molecular weight distribution, and is consequently suitable for blow molding and extrusion molding. Thus, polyethylene produced by the Phillips catalyst has a relatively wide molecular weight distribution and has a high melt tension, it is widely produced typically as a resin for a blow molding method.

Such a resin is desired to be further improved in respect of ESCR and creep resistance, but a satisfactory industrial production method which satisfy both ESCR and creep resistance at the same time has not been proposed up to now.

In order to improve ESCR or creep resistance of an ethylene polymer, multistage polymerization using a Ziegler catalyst or a metallocene catalyst is carried out. For example, in a case of two stage polymerization using a Ziegler catalyst or a metallocene catalyst, ethylene and α-olefin are copolymerized to form a high molecular weight component in the first stage, and a low molecular weight component is formed by introducing hydrogen of a chain transfer agent in the second stage, and consequently a method for producing an ethylene polymer having a wide molecular weight distribution is often carried out. According to this method, a short chain branch derived from α-olefin is introduced into a high molecular chain of a high molecular weight component, thereby improving ESCR and creep resistance properties. Particularly, in a case of using a metallocene catalyst, a short chain branch is uniformly introduced, and consequently, ESCR or creep resistance is more effectively improved. In the low molecular weight component of the second stage, only a small amount of a short chain branch derived from α-olefin flown without being consumed in the first stage is introduced, and therefore a polymer having a high density and an improved rigidity can be obtained. This two stage polymerization method does not require an intermediate flush tank between the first stage and the second stage, and is therefore preferable in respect of productivity. Since the ethylene polymer obtained by this method has satisfactory ESCR and creep resistance, it is widely acceptable in the market.

Also, it has been tried to improve ESCR or creep resistance by using a chromium catalyst in multistage polymerization, but has not been satisfactory on the following grounds. That is, in the case of a chromium catalyst, if an activation temperature of the catalyst is determined, the control of a molecular weight is carried out only by the control of a polymerization temperature, but there is a limit that the polymerization temperature can not be higher than a temperature at which polyethylene particles formed by slurry polymerization initiate to dissolve in a solvent. Therefore, it is convenient if a molecular weight can be reduced by adding hydrogen in the same manner as in a case of using a Ziegler catalyst or a metallocene catalyst, but in the case of a chromium catalyst, hydrogen hardly works as a chain transfer agent and it is hard to obtain a lower molecular weight even when adding hydrogen.

Therefore, in the case of using a chromium catalyst, even when carrying out multistage polymerization, it is difficult to make a molecular weight distribution so wide as to be able to improve ESCR or creep resistance. So, in the case of a chromium catalyst, introduction of a short chain branch is not uniform as compared with a Ziegler catalyst or a metallocene catalyst, and therefore α-olefin flown from the first stage to the second stage copolymerizes also in the second stage, and consequently a short chain branch is introduced into a low molecular weight zone in a low molecular weight component and the improvement of ESCR or creep resistance is not sufficient when compared at the same level of density. Therefore, in the multistage polymerization of ethylene simply using a conventional chromium catalyst, it is difficult to make a molecular weight distribution so wide as to improve ESCR or creep resistance.

Accordingly, there has been heretofore proposed a method for modifying or denaturing by employing a system of a combination of a chromium catalyst and an organoaluminum compound. However, in the system of employing a conventional organoaluminum compound, the denaturing or the modification has not been satisfactory. Thus, in the case of using a conventionally proposed organoaluminum compound, hydrogen easily works as a chain transfer agent, and an effect of forming a low molecular weight by adding hydrogen can be recognized. However, in the case of using the conventional organoaluminum compound, α-olefin is byproduced, and the byproduced α-olefin or α-olefin separately added easily copolymerizes with ethylene, and therefore a density of polyethylene obtained by adding the conventional organoaluminum compound is likely to be easily lowered.

A method for improving both ESCR and creep resistance at the same time is illustrated, for example, as described below.

1) It can be expected that ESCR of polyethylene can be improved to some extent by mixing a higher molecular weight component and a lower molecular weight component without exhibiting a bimodal in a molecular weight distribution obtained by GPC (gel permeation chromatograph) measurement of a finally obtained polyethylene. It is expected that the degree of ESCR improvement is increased as the molecular weight distribution becomes wider.

2) Since the above polyethylene can be easily produced by multistage polymerization, it is preferable to employ a method for continuously polymerizing by arranging a plurality of polymerization reactors not in parallel but in series, the reaction of which can be easily adjusted as compared with the parallel type arrangement, and a continuous system is more efficient than the batch system.

3) It is not always easy to uniformly mix both components of a high molecular weight component and a low molecular weight component. In order to uniformly blend, a high molecular weight component is first produced and a low molecular weight component is then produced continuously by multistage polymerization arranged in series using a transition metal-supported catalyst, thereby likely to produce a uniform mixture of both high and low molecular weight components. This method is particularly preferable when using a transition metal-supported catalyst carrying a transition metal on an inorganic support. A chromium type catalyst often used in the production of polyethylene resin usable for a large molded product, is designed in such a manner as to produce a high molecular weight resin for improving mechanical properties, but it is hard to uniformly mix due to its high molecular weight. Therefore, it is required that the chromium type catalyst provides a resin having a more uniform molecular weight.

4) A method for adjusting a molecular weight by using hydrogen is convenient. However, since hydrogen introduced into the polymerization system is not basically consumed and its certain amount remains, the remaining hydrogen supplied to a reactor is likely to influence on the polymerization reaction in other polymerization reactors in the continuous production method. Therefore, when adjusting a molecular weight by using hydrogen in the multistage polymerization, it is preferable not to substantially supply hydrogen to the first stage reactor but to supply to another stage. Since it is preferable to produce a high molecular weight component at the first stage (a low molecular weight component is produced at the latter stage) due to the requirement of producing such a resin having a uniform molecular weight as described above, it is preferable to employ a catalyst system which lowers a molecular weight by the presence of hydrogen introduced at the latter stage. Also, in the case of a Phillips catalyst, it is easy to produce a high molecular weight component, but it is difficult to produce a low molecular weight component due to the difficulty of chain transfer of hydrogen as far as a slurry polymerization method is employed.

5) In order to improve both of ESCR and creep resistance at the same time, it is important to selectively introduce a branch into a high molecular weight component by a comonomer. Therefore, it is necessary to introduce a comonomer into a specific stage of multistage polymerization. Since it is preferable to produce a high molecular weight component at the first stage as described above, introduction of a comonomer for imparting a branch is made at the first polymerization stage and it is preferable not to introduce a branch at the latter stage. In the continuous production method, it is expected that a remaining comonomer flows into the latter stage but a predetermined amount of a comonomer is already consumed at the first stage and the remaining comonomer is reduced and has less influence. However, if a catalyst used in such a reactor as the second stage reactor wherein a comonomer remains, has less polymerizability with ethylene and α-olefin, the flown remaining comonomer does not practically copolymerize with a comonomer and it is therefore considered that the remaining comonomer is less influential. Accordingly, it is more preferable if a catalyst having a low copolymerizability in reactors after the first stage is used.

6) Mechanical properties of a resin are generally improved if its molecular weight is made higher, but on the other hand, its molding processibility is lowered. Therefore, it is generally preferable for designing and developing a resin material in such a manner as to secure a predetermined molding processibility and to obtain a component having a higher molecular weight.

The above-described methods are considered as an industrial production method for improving both ESCR and creep resistance at the same time.

As such a method relating to a prior art as described above, JP-A-57-70109 discloses polymerization of ethylene by a chromium catalyst in the presence of specific two kinds of organoaluminum compounds in two different reaction zones of A and B. In this method, a low molecular weight component is produced by introducing hydrogen in coexistence with two kinds of specific organoaluminum compounds, and it is possible to improve ESCR to some extent, but it is not always possible to obtain a component having a sufficiently low molecular weight. Thus, it is hardly regarded as an industrial production method for improving both of ESCR and creep resistance at the same time.

Also, as a concrete method (example), a method suitable for a continuous production method is employed, wherein polymerization is first carried out by introducing a certain organoaluminum compound, and another reforming agent is introduced for reforming and polymerization is further reopened. All of the disclosed examples first produce a low molecular weight component liable to increase ununiformity of a resin statistically obtained. Thus, a method of this patent publication is hardly regarded as an industrial production method for improving both of ESCR and creep resistance at the same time.

JP-A-11-189602 discloses a method for improving ESCR of an ethylene polymer by two stage polymerization using a chromium catalyst. However, this method also employs a conventional general chromium catalyst having the above-mentioned problems, and is not a method using a chromium catalyst capable of producing a low molecular weight component and is not expected to improve ESCR to an industrially sufficient level.

JP-B-47-23176, JP-B-51-3360, JP-B-3-23564, JP-A-51-17993 and International Patent Publication WO94/13708 disclose a method for producing a low molecular weight component by enhancing a chain transfer ability of hydrogen by combining a chromium catalyst with a dialkylaluminum alkoxide or dialkylaluminum phenoxide as an organoaluminum compound. However, such a method can produce a low molecular weight component, but this can not be an industrial production method for improving both of ESCR and creep resistance at the same time as mentioned above.

JP-B-47-1365 and JP-B-49-13230 disclose a method for producing a low molecular weight component by enhancing a chain transfer ability of hydrogen by combining a chromium catalyst with a dialkylaluminum siloxide as an organoaluminum compound. Also, JP-A-2000-86718 and JP-A-2000-198811 disclose a method for adjusting a molecular weight by hydrogen by combining a chromium catalyst with an alkoxy group or phenoxy group-containing organoaluminum compound.

These methods also can produce a low molecular weight component, but this methods alone can not be an industrial production method for improving both of ESCR and creep resistance at the same time.

JP-A-58-96606 discloses a catalyst comprising a combination of a chromium catalyst and an organoaluminum compound having both an alkoxy group and a hydrosiloxy group. This catalyst has a disadvantage of byproducing α-olefin comprising 1-hexene as the main component and introducing a short chain branch into a low molecular weight component, and is therefore clearly poor in respect of ESCR and creep resistance at the same density as compared with the case of having no branch in a low molecular weight component.

JP-A-2001-294613 discloses an ethylene polymerization catalyst obtained by treating a chromium catalyst with an organoaluminum compound having both an alkoxy group and a hydrosiloxy group and further using an organoaluminum alkoxide. This method prevents by-production of α-olefin comprising 1-hexene as the main component, but is complicated since a plurality of kinds of organoaluminum compounds are used. Also, this publication does not disclose two stage polymerization.

SUMMARY OF THE INVENTION

An object of the present invention is to provide an ethylene polymer excellent in ESCR and creep resistance and a method for producing the same.

The present inventors have intensively studied the above object, and discovered that an ethylene polymer excellent in both ESCR and creep resistance can be obtained by producing an ethylene polymer by multistage polymerization using a chromium catalyst and a specific organoaluminum compound. The present invention has been accomplished on the basis of this discovery.

Thus, the above object can be achieved by providing a method for producing an ethylene polymer (Features 1 to 10), an ethylene polymer (Feature 11), its molded articles (Features 12 and 13), a novel organoaluminum compound (Feature 14), an ethylene polymerization catalyst comprising a chromium catalyst and a specific organoaluminum compound (Features 15 to 16), and a method for producing an ethylene polymer by polymerization with the above catalyst system (Feature 17).

Feature 1. A method for producing an ethylene polymer which comprises continuously polymerizing ethylene alone or copolymerizing ethylene and a $C_3$-$C_8$ α-olefin by multi-stage polymerization in a plurality of polymerization reactors connected in series in the presence of a chromium catalyst having at least a part of chromium atoms converted to hexavalent chromium supported on an inorganic oxide support by calcination-activating in a non-reducing atmosphere, wherein an organoaluminum compound of the formula (1):

(in the above formula, $R^1$ and $R^2$ may be the same or different, each represents a $C_1$-$C_{18}$ alkyl group, a $C_6$-$C_{18}$ aryl group, $C_7$-$C_{18}$ aryl-substituted alkyl group or $C_7$-$C_{18}$ alkyl-substituted aryl group, $R^3$, $R^4$ and $R^5$ may be the same or different, each represents a $C_1$-$C_{18}$ alkyl group or a $C_6$-$C_{18}$ aryl group, $R^1$, $OR^2$ and $OSiR^3R^4R^5$ respectively may be the same or different when each has a plurality of kinds, and x, y and z are respectively $0 \leq x \leq 3$, $0 \leq y \leq 3$, $0 \leq z < 3$, and $x+y+z=3$) is introduced at least one or all of the polymerization reactors.

Feature 2. The method for producing an ethylene polymer according to Feature 1, wherein the organoaluminum compound is introduced into any of the second or succeeding stages of the plurality of polymerization reactors connected in series.

Feature 3. The method for producing an ethylene polymer according to Feature 1 or 2, wherein hydrogen is introduced into optional any of the polymerization reactors connected in series.

Feature 4. The method for producing an ethylene polymer according to Feature 3, wherein hydrogen is introduced into the second or succeeding polymerization reactors, in which the organoaluminum compound is introduced or is present by flowing therein.

Feature 5. The method for producing an ethylene polymer according to any one of Features 1 to 4, wherein the $C_3$-$C_8$ α-olefin is introduced into the first stage polymerization reactor of a plurality of polymerization reactors connected in series and is not substantially introduced into the second and succeeding polymerization reactors.

Feature 6. A method for producing an ethylene polymer, which comprises continuously copolymerizing ethylene and a $C_3$-$C_8$ α-olefin in a plurality of reaction zones connected in series in the presence of a chromium catalyst having at least a part of chromium atoms converted to hexavalent chromium supported on an inorganic oxide support by calcination-activating in a non-reducing atmosphere and which includes the following steps (1) to (4):

(1) step of copolymerizing ethylene and the α-olefin in a slurry state by introducing the chromium catalyst, ethylene, the α-olefin and a reaction solvent into the first reaction zone, (2) step of withdrawing a part or all of a reaction mixture including the catalyst and the reaction medium from the reaction zone and transferring into a next reaction zone, (3) step of continuing the slurry polymerization by introducing hydrogen, an organoaluminum compound having the formula (1),

(in the above formula, $R^1$, $R^2$, $R^3$, $R^4$ and $R^5$ are the same as defined in Feature 1), and ethylene into the reaction zone, to which the reaction mixture is transferred, and (4) step of withdrawing the reaction mixture from the reaction zone to obtain an ethylene polymer.

Feature 7. A method for producing an ethylene polymer, which comprises continuously copolymerizing ethylene and a $C_3$-$C_8$ α-olefin in a plurality of reaction zones arranged in series in the presence of a chromium catalyst having at least a part of chromium atoms converted to hexavalent chromium supported on an inorganic oxide support by calcination-activating in a non-reducing atmosphere and which includes the following steps (1) to (4):

(1) step of copolymerizing ethylene and the α-olefin in a slurry state by introducing the chromium catalyst, an organoaluminum compound having the formula (1),

(in the above formula, $R^1$, $R^2$, $R^3$, $R^4$ and $R^5$ are the same as defined in Feature 1), ethylene, the α-olefin and a reaction solvent into the first reaction zone, (2) step of withdrawing a part or all of a reaction mixture including the catalyst, the organoaluminum compound and the reaction solvent from the reaction zone and transferring into a next reaction zone, (3) step of continuing the slurry polymerization by introducing hydrogen and ethylene into the reaction zone, to which the reaction mixture is transferred, and (4) step of withdrawing the reaction mixture from the reaction zone to obtain an ethylene polymer.

Feature 8. The method for producing an ethylene polymer according to Feature 1, 6 or 7, wherein the organoaluminum compound having the formula (1) is expressed by the following formula (2), (3) or (4),

(in the above formula, $R^6$ and $R^7$ may be the same or different, each represents a $C_1$-$C_{18}$ alkyl group, $R^8$, $R^9$ and $R^{10}$ may be the same or different, and each represents a hydrogen atom, a $C_1$-$C_{17}$ alkyl group or a $C_6$-$C_{17}$ aryl group, provided that the total carbon number of $R^8$, $R^9$ and $R^{10}$ is at most 17), $$R^{11}R^{12}Al(OSiR^{13}R^{14}R^{15}) \quad (3)$$

(in the above formula, $R^{11}$ and $R^{12}$ may be the same or different, each represents a $C_1$-$C_{18}$ alkyl group, $R^{13}$, $R^{14}$ and $R^{15}$ may be the same or different, and each represents a $C_1$-$C_{18}$ alkyl group or a $C_6$-$C_{18}$ aryl group, provided that the total carbon number of $R^{13}$, $R^{14}$ and $R^{15}$ is at most 18), or $$R^{16}R^{17}Al(OC_6R^{18}R^{19}R^{20}R^{21}R^{22}) \quad (4)$$

(in the above formula, $R^{16}$ and $R^{17}$ may be the same or different, each represents a $C_1$-$C_{18}$ alkyl group, $C_6R^{18}R^{19}R^{20}R^{21}R^{22}$ represents phenyl group or substituted phenyl group, $R^{18}$, $R^{19}$, $R^{20}$, $R^{21}$ and $R^{22}$ may be the same or different, and each represents a hydrogen atom or a $C_1$-$C_{12}$ alkyl group, provided that the total carbon number of $R^{18}$, $R^{19}$, $R^{20}$, $R^{21}$ and $R^{22}$ is at most 12).

Feature 9. The method for producing an ethylene polymer according to Feature 8, wherein an organoaluminum compound having the formula (2) is expressed by the following formula (5), $$R^{23}R^{24}Al(OCHR^{25}R^{26}) \quad (5)$$

(in the above formula, $R^{23}$ and $R^{24}$ may be the same or different, each represents a $C_1$-$C_{18}$ alkyl group, $R^{25}$ and $R^{26}$ may be the same or different, and each represents a hydrogen atom or a $C_1$-$C_{17}$ alkyl group, provided that the total carbon number of $R^{25}$ and $R^{26}$ is at most 17).

Feature 10. A method for producing an ethylene polymer according to any one of Features 1 to 9, wherein an ethylene polymer having an HLMFR value of from 1 to 100 g/10 minutes and a density of from 0.930 to 0.970 g/cm³ is obtained.

Feature 11. An ethylene polymer having an HLMFR value of from 1 to 100 g/10 minutes and a density of from 0.930 to 0.970 g/cm³ obtained by the method for producing an ethylene polymer as defined in any one of Features 1 to 10.

Feature 12. Blow-molded articles obtained by blow-molding the ethylene polymer as defined in Feature 11.

Feature 13. Extrusion-molded articles obtained by extrusion-molding the ethylene polymer as defined in Feature 11.

Feature 14. An organoaluminum compound having the formula (101), $$(R^{101})_xAl(OR^{102})_y(OSiR^{103}R^{104}R^{105})_z \quad (101)$$

(in the above formula, $R^{101}$ and $R^{102}$ may be the same or different, each represents a $C_1$-$C_{18}$ alkyl group, $R^{103}$, $R^{104}$ and $R^{105}$ may be the same or different, each represents a $C_1$-$C_{18}$ alkyl group or a $C_6$-$C_{18}$ aryl group, at least one of $R^{103}$, $R^{104}$ and $R^{105}$ is an alkyl group, and x, y and z are respectively $0.5 \leq x \leq 2$, $0.5 \leq y \leq 2$, $0.5 \leq z \leq 2$, and $x+y+z=3$).

Feature 15. A catalyst for producing an ethylene polymer, which comprises a chromium catalyst having at least a part of chromium atoms converted to hexavalent chromium obtained by calcination-activating a chromium compound supported on an inorganic oxide support in a non-reducing atmosphere and an organoaluminum compound having the formula (102), $$(R^{101})_xAl(OR^{102})_y(OSiR^{103}R^{104}R^{105})_z \quad (102)$$

(in the above formula, $R^{101}$, $R^{102}$, $R^{103}$, $R^{104}$ and $R^{105}$ may be the same or different, each represents a $C_1$-$C_{18}$ hydrocarbon residue, and x, y and z are respectively $0<x<3$, $0<y<3$, $0<z<3$, and $x+y+z=3$).

Feature 16. A catalyst for producing an ethylene polymer according to Feature 15, wherein the organoaluminum compound is represented by the formula (103), $$(R^{101})_xAl(OR^{102})_y(OSiR^{103}R^{104}R^{105})_z \quad (103)$$

(in the above formula, $R^{101}$ and $R^{102}$ may be the same or different, each represents a $C_1$-$C_{18}$ alkyl group, $R^{103}$, $R^{104}$ and $R^{105}$ may be the same or different, each represents a $C_1$-$C_{18}$ alkyl group or a $C_6$-$C_{18}$ aryl group, at least one of $R^{103}$, $R^{104}$ and $R^{105}$ is an alkyl group, and x, y and z are respectively $0.5 \leq x \leq 2$, $0.5 \leq y \leq 2$, $0.5 \leq z \leq 2$, and $x+y+z=3$).

Feature 17. A method for producing an ethylene polymer, which comprises polymerizing ethylene or copolymerizing ethylene and other monomer in the presence of the catalyst as defined in Feature 15.

DETAILED DESCRIPTION OF THE PREFERRED EMBODIMENTS

Hereinafter, the present invention is described in more details.

(Chromium Catalyst)

A chromium catalyst having at least a part of chromium atoms converted to hexavalent chromium supported on an organic oxide support by calcination-activating in a non-reducing atmosphere, is known as a catalyst for producing an ethylene polymer (generally referred to as "Phillips catalyst"). For example, the outline of this catalyst is described in the literature "Advances in Catalysis" by M. P. McDaniel (Volume 33, p. 47, 1985).

An inorganic oxide support used for the above chromium catalyst is preferably an oxide of a metal of Group 2, 4, 13 or 14 of the Periodic Table. Examples include magnesia, titania, zirconia, alumina, silica, thoria, silica-titania, silica-zirconia, silica-alumina or a mixture thereof. Among them, silica, silica-titania, silica-zirconia and silica-alumina are preferable. In the case of silica-titania, silica-zirconia and silica-alumina, titanium, zirconium or aluminum atom is contained as a metal component other than silica in an amount of from 0.2 to 10 mass %, preferably from 0.5 to 7 mass %, more preferably from 1 to 5 mass %. A method for preparing a support suitable for these chromium catalysts, their physical properties and features are described in "Preparation of Catalysts" by C. E. Marsden (Volume V, p. 215, 1991), "Plastics, Rubber and Composites Processing and Applications" by C. E. Marsden, Elsevier Science Publishers (Volume 21, p. 193, 1994), and the like.

A specific surface area of these inorganic oxide support is from 100 to 1,000 m²/g, preferably from 150 to 800 m²/g, more preferably from 200 to 600 m²：/g.

Their pore volume is from 0.5 to 3.0 cm³/g, preferably from 0.7 to 2.7 cm³/g, more preferably from 1.0 to 2.5 cm³/g. Their average particle size is from 10 to 200 µm, preferably from 20 to 150 µm, more preferably from 30 to 100 µm.

A chromium compound is supported on the above inorganic oxide support. The chromium compound thus supported is a compound, at least a part of chromium atoms is converted to hexavalent by calcination-activation in a non-reducing atmosphere. Examples of the chromium compound include chromium oxide, chromium halide, chromium oxyhalide, chromate, bichromate, chromium nitrate, chromium carboxylate, chromium sulfate, chrom-1,3-diketo compound, chromic acid ester, and the like. Their concrete examples include chromium trioxide, chromium trichloride, chromyl chloride, potassium chromate, ammonium chromate, potassium bichromate, chromium nitrate, chromium sulfate, chromium acetate, tris(2-ethylhexanoate)chromium, chromium acetylacetonate, bis(tert-butyl)chromate, and the like. Among them, chromium trioxide, chromium nitrate, chromium acetate and chromium acetylacetonate are preferable. Even in the case of using a chromium compound having an organic group such as chromium acetylacetonate and chromium acetate, the organic group part is burned by calcination-activation in a non-reducing atmosphere as mentioned below, and it is reacted with a hydroxyl group of a surface of an inorganic oxide support in the same manner as in the case of chromium trioxide, and at least a part of chromium atoms is converted to hexavalent to be fixed as a chromic acid ester structure.

Examples of a method for supporting a chromium compound on an inorganic oxide support include well known various methods including impregnation, distillation of solvent, sublimation and the like. An amount of the chromium compound to be supported is from 0.2 to 2.0 mass %, preferably from 0.3 to 1.7 mass %, more preferably from 0.5 to 1.5 mass %, as a chromium atom to a carrier.

After supporting a chromium compound, it is subjected to activation treatment by calcination. The calcination-activating treatment is carried out in a non-reducing atmosphere containing substantially no water content, such as oxygen or air. An inert gas may also be present at this time. The calcination-activating treatment is preferably carried out by using air sufficiently dried by passing through a molecular sieve and is carried out in a fluidized state. The calcination-activation is carried out at temperature of from 400 to 900° C., preferably from 450 to 850° C., more preferably from 500 to 800° C. for 30 minutes to 48 hours, preferably 1 hour to 24 hours, more preferably 2 hours to 12 hours. At least a part of chromium atoms of a chromium compound supported on an inorganic oxide support is oxidized to hexavalent and is chemically fixed on the support by the calcination-activating treatment.

In accordance with the above-mentioned method, a chromium catalyst used in the present invention can be obtained, but before supporting a chromium compound or after supporting the chromium compound, and before the calcination-activating treatment, metal alkoxides or organometallic compounds represented by titanium alkoxides such as titanium tetraisopropoxide, zirconium alkoxides such as zirconium tetrabutoxide, aluminum alkoxides such as aluminum tributoxide, organoaluminums such as trialkylaluminum, organic magnesiums such as dialkylmagnesium or the like, or fluorine-containing salts such as ammonium fluorosilicate, may be added in order to adjust ethylene polymerization activity, copolymerizability with α-olefin, a molecular weight or a molecular weight distribution of an ethylene polymer to be obtained, and the like in accordance with a well known method.

These metal alkoxides or organometallic compounds are subjected to calcination-activating treatment in a non-reducing atmosphere to burn an organic group part, and are oxidized to a metal compound such as titania, zirconia, alumina or magnesia to be contained in the catalyst. Also, in the case of fluorine-containing salts, an organic oxide support is fluorinated. These methods are described in "Plastics, Rubber and Composites Processing and Applications" by C. E. Marsden, (Volume 21, p. 193, 1994), and the like.

(Organoaluminum Compound)

An organoaluminum compound used in the present invention is a compound expressed by the following formula (1).

$$(R^1)_x Al(OR^2)_y (OSiR^3R^4R^5)_z \tag{1}$$

(in the above formula, $R^1$ and $R^2$ may be the same or different, each represents a $C_1$-$C_{18}$ alkyl group, a $C_6$-$C_{18}$ aryl group, $C_7$-$C_{18}$ aryl-substituted alkyl group or a $C_7$-$C_{18}$ alkyl-substituted aryl group, $R^3$, $R^4$ and $R^5$ may be the same or different, each represents a $C_1$-$C_{18}$ alkyl group or a $C_6$-$C_{18}$ aryl group, $R^1$, $OR^2$ and $OSiR^3R^4R^5$ respectively may be the same or different when each has a plurality of kinds, and x, y and z are respectively $0 \leq x \leq 3$, $0 \leq y < 3$, $0 \leq z < 3$, and $x+y+z=3$).

The compound expressed by the above formula (1) may be used alone or a mixture of two or more kinds.

By introducing at least one kind of the compound of the formula (1) into a polymerization reactor by Phillips catalyst, the catalyst system realizes a response to hydrogen. Thus, a chain transfer capability of the chromium catalyst to hydrogen is raised, and it becomes possible to lower a molecular weight by introducing hydrogen. Accordingly, in multistage polymerization by Phillips catalyst, by introducing the compound of the formula (1) into the polymerization stage (polymerization reactor) aiming at polymerization of a low molecular weight component and appropriately introducing hydrogen in combination therewith, a molecular weight can be easily and conveniently lowered. Also, even by adding the compound of the formula (1), the catalyst efficiency of Phillips catalyst is not lowered and is rather improved, thus achieving easily the aimed effect by multistage polymerization.

Among the compounds of the formula (1), the compounds of the following formulae (2), (3) and (4) are preferable.

A dialkylaluminum alkoxide of the formula (2), $$R^6 R^7 Al(OCR^8 R^9 R^{10}) \tag{2}$$

(in the above formula, $R^6$ and $R^7$ may be the same or different, each represents a $C_1$-$C_{18}$ alkyl group, $R^8$, $R^9$ and $R^{10}$ may be the same or different, and each represents a hydrogen atom, a $C_1$-$C_{17}$ alkyl group or a $C_6$-$C_{17}$ aryl group, provided that the total carbon number of $R^8$, $R^9$ and $R^{10}$ is at most 17);

a dialkylaluminum siloxide of the formula (3), $$R^{11} R^{12} Al(OSiR^{13} R^{14} R^{15}) \tag{3}$$

(in the above formula, $R^{11}$ and $R^{12}$ may be the same or different, each represents a $C_1$-$C_{18}$ alkyl group, $R^{13}$, $R^{14}$ and $R^{15}$ may be the same or different, and each represents a $C_1$-$C_{18}$ alkyl group or a $C_6$-$C_{18}$ aryl group, provided that the total carbon number of $R^{13}$, $R^{14}$ and $R^{15}$ is at most 18); and a dialkylaluminum phenoxide of the formula (4), $$R^{16} R^{17} Al(OCR^{18} R^{19} R^{20} R^{21} R^{22}) \tag{4}$$

(in the above formula, $R^{16}$ and $R^{17}$ may be the same or different, each represents a $C_1$-$C_{18}$ alkyl group, $C_6 R^{18} R^{19} R^{20} R^{21} R^{22}$ represents phenyl group or substituted phenyl group, $R^{18}$, $R^{19}$, $R^{20}$, $R^{21}$ and $R^{22}$ may be the same or different, and each represents a hydrogen atom or a $C_1$-$C_{12}$ alkyl group, provided that the total carbon number of $R^{18}$, $R^{19}$, $R^{20}$, $R^{21}$ and $R^{22}$ is at most 12).

In the alkylaluminum alkoxide of the formula (2), examples of $R^6$ and $R^7$ include methyl, ethyl, n-propyl, i-propyl, n-butyl, i-butyl, sec-butyl, tert-butyl, n-hexyl, n-octyl, n-decyl, n-dodecyl, cyclohexyl or the like, and methyl, ethyl, n-butyl, i-butyl, n-hexyl or n-octyl is preferable, and among them, methyl, ethyl, n-butyl or i-butyl is particularly preferable. Also, examples of $R^8$, $R^9$ and $R^{10}$ include hydrogen, methyl, ethyl, n-propyl, i-propyl, n-butyl, i-butyl, sec-butyl, tert-butyl, n-pentyl, n-heptyl, n-nonyl, n-undecyl, cyclohexyl, phenyl, naphthyl or the like, and hydrogen, methyl, ethyl, n-propyl, i-propyl, n-butyl, i-butyl, sec-butyl, tert-butyl, n-pentyl or n-heptyl is preferable, and among them, hydrogen, methyl, ethyl, n-propyl or i-propyl is particularly preferable.

Examples of the dialkylaluminum alkoxide of the formula (2) include dimethylaluminum methoxide, diethylaluminum methoxide, di-n-butylaluminum methoxide, di-i-butylaluminum methoxide, dimethyaluminum ethoxide, diethylaluminum ethoxide, di-n-butylaluminum ethoxide, di-i-butylaluminum ethoxide, dimethylaluminum n-propoxide, diethylaluminum n-propoxide, di-n-butylaluminum n-propoxide, di-i-butylaluminum n-propoxide, dimethylaluminum i-propoxide, diethylaluminum i-propoxide, di-n-butylaluminum i-propoxide, di-i-butylaluminum i-propoxide, dimethylaluminum n-butoxide, diethylaluminum n-butoxide, di-n-butylaluminum n-butoxide, di-i-butylaluminum n-butoxide, dimethylaluminum i-butoxide, diethylaluminum i-butoxide, di-n-butylaluminum i-butoxide, di-i-butylaluminum i-butoxide or the like, and among them, dimethylaluminum ethoxide, diethylaluminum ethoxide, di-n-butylaluminum ethoxide or di-i-butylaluminum ethoxide is preferable.

In the dialkylaluminum siloxide of the formula (3), examples of $R^{11}$ and $R^{12}$ include methyl, ethyl, n-propyl, i-propyl, n-butyl, i-butyl, sec-butyl, tert-butyl, n-hexyl, n-octyl, n-decyl, n-dodecyl, cyclohexyl or the like, and methyl, ethyl, n-butyl, i-butyl, n-hexyl or n-octyl is preferable, and among them, methyl, ethyl, n-butyl or i-butyl is particularly preferable. Example of $R^{13}$, $R^{14}$ and $R^{15}$ include methyl, ethyl, n-propyl, i-propyl, n-butyl, i-butyl, sec-butyl, tert-butyl, n-hexyl, n-octyl, n-decyl, n-dodecyl, cyclohexyl, phenyl, naphthyl or the like, and methyl, ethyl or i-propyl is preferable, and among them, methyl or ethyl is particularly preferable.

Examples of the dialkylaluminum siloxide of the formula (3) include dimethylaluminum trimethylsiloxide, dimethylaluminum triethylsiloxide, diethylaluminum trimethylsiloxide, diethylaluminum triethylsiloxide, di-n-butylaluminum trimethylsiloxide, di-n-butylaluminum triethylsiloxide, di-i-butylaluminum trimethylsiloxide, di-i-butylaluminum triethylsiloxide or the like, and among them, dimethylaluminum trimethylsiloxide, dimethylaluminum triethylsiloxide, di-n-butylaluminum trimethylsiloxide, or di-i-butylaluminum trimethylsiloxide is preferable.

In the dialkylaluminum phenoxide of the formula (4), examples of $R^{16}$ and $R^{17}$ include methyl, ethyl, n-propyl, i-propyl, n-butyl, i-butyl, sec-butyl, tert-butyl, n-hexyl, n-octyl, n-decyl, n-dodecyl, cyclohexyl or the like, and methyl, ethyl, n-butyl, i-butyl, n-hexyl or n-octyl is preferable, and among them, methyl, ethyl, n-butyl or i-butyl is particularly preferable. Also, examples of $R^{18}$, $R^{19}$, $R^{20}$, $R^{21}$ and $R^{22}$ include hydrogen, methyl, ethyl, n-propyl, i-propyl, n-butyl, i-butyl, sec-butyl, tert-butyl, n-hexyl, n-octyl, n-decyl, n-dodecyl, cyclohexyl or the like, and hydrogen, methyl or ethyl is preferable, and among them, hydrogen or methyl is particularly preferable.

Examples of the dialkylaluminum phenoxide of the formula (4) include dimethylaluminum phenoxide, dimethylaluminum 4-methylphenoxide, dimethylaluminum 2,6-dimethylphenoxide, dimethylaluminum 2,4,6-trimethylphenoxide, diethylaluminum phenoxide, diethylaluminum 4-methylphenoxide, diethylaluminum 2,6-dimethylphenoxide, diethylaluminum 2,4,6-trimethylphenoxide, di-n-butylaluminum phenoxide, di-n-butylaluminum 4-methylphenoxide, di-n-butylaluminum 2,6-dimethylphenoxide, di-n-butylaluminum 2,4,6-trimethylphenoxide, di-i-butylaluminum phenoxide, di-i-butylaluminum 4-methylphenoxide, di-i-butylaluminum 2,6-dimethylphenoxide, di-i-butylaluminum 2,4,6-trimethylphenoxide or the like, and among them, diethylaluminum phenoxide, diethylaluminum 4-methylphenoxide, diethylaluminum 2,6-dimethylphenoxide or diethylaluminum 2,4,6-trimethylphenoxide is preferable.

Among the above organoaluminum compounds, the organoaluminum of the formula (2) or (3) is preferable in respect that a chain transfer capability of the chromium catalyst to hydrogen is enhanced, and the organoaluminum compound of the formula (2) is particularly preferable.

Also, if the organoaluminum compound of the formula is used in combination with a Phillips catalyst, there is a case that a branch resulted from α-olefin by-produced from ethylene is imparted to a resin. As explained above, since it is preferable to selectively impart a branch to a high molecular weight component, it is preferable that an amount of the branch to be imparted is small when the organoaluminum compound of the present invention is used in combination with a Phillips catalyst. Thus, in the catalyst system of the present invention, it is preferable that an amount of α-olefin byproduced is small, and that even if α-olefin is byproduced, copolymerizability of α-olefin and ethylene is low. As this result, copolymerizability of a comonomer such as α-olefin is lowered, and a high density product is preferably easily obtainable. From this viewpoint, it is a dialkylaluminum alkoxide of the following formula (5) that is preferable among the dialkylaluminum alkoxides of the above formula (2).

Further, when the organoaluminum compound of the present invention is combined with a chromium catalyst, there is a case that α-olefin is byproduced from ethylene, and there is a case that a physical property-improving effect is unsatisfactory even when widening a molecular weight distribution by hydrogen by enhancing a chain transfer capability of the chromium catalyst to hydrogen. From this viewpoint also, the dialkylaluminum alkoxide of the formula (5) is preferable.

$$R^{23}R^{24}Al(OCHR^{25}R^{26}) \tag{5}$$

(in the above formula, $R^{23}$ and $R^{24}$ may be the same or different, each represents a $C_1$-$C_{18}$ alkyl group, $R^{25}$ and $R^{26}$ may be the same or different, and each represents a hydrogen atom or a $C_1$-$C_{17}$ alkyl group, provided that the total carbon number of $R^{25}$ and $R^{26}$ is at most 17).

In the dialkylaluminum alkoxide of the formula (5), examples of $R^{23}$ and $R^{24}$ include methyl, ethyl, n-propyl, i-propyl, n-butyl, i-butyl, sec-butyl, tert-butyl, n-hexyl, n-octyl, n-decyl, n-dodecyl, cyclohexyl or the like, and methyl, ethyl, n-butyl, i-butyl, n-hexyl or n-octyl is preferable, and among them, ethyl, n-butyl or i-butyl is particularly preferable. Also, examples of $R^{25}$, and $R^{25}$ include hydrogen, methyl, ethyl, n-propyl, i-propyl, n-butyl, i-butyl, sec-butyl, tert-butyl, n-pentyl, n-heptyl, n-nonyl, n-undecyl, cyclohexyl or the like, and hydrogen, methyl, ethyl, n-propyl, i-propyl, n-butyl or i-butyl is preferable, and among them, hydrogen, methyl, ethyl or n-propyl is particularly preferable.

Concrete examples of the dialkylaluminum alkoxide of the formula (5) include diethylaluminum methoxide, di-n- butylaluminum methoxide, di-i-butylaluminum methoxide, dimethylaluminum ethoxide, di-n-butylaluminum ethoxide, di-butylaluminum ethoxide, diethylaluminum n-propoxide, di-n-butylaluminum n-propoxide, di-n-butylaluminum n-propoxide, diethylaluminum i-propoxide, di-n-butylaluminum i-propoxide, di-i-butylaluminum i-propoxide, diethylaluminum n-butoxide, di-n-butylaluminum n-butoxide, di-i-butylaluminum n-butoxide or the like, and among them, diethylaluminum ethoxide, di-n-butylaluminum ethoxide or di-i-butylaluminum ethoxide is preferable.

The organoaluminum compound used in the present invention may be commercially available ones, or can be easily prepared by reacting a trialkylaluminum with alcohols, silanols, and/or phenols respectively.

For example, the dialkylaluminum alkoxide of the formula (2) can be prepared by reacting a trialkylaluminum with its corresponding alcohols at a mol ratio of 1:1 in accordance with the following reaction step formula (in the reaction step, R may be the same or different from $R^6$ or $R^7$, and is a $C_1$-$C_{18}$ alkyl group, and $R^6$ to $R^{10}$ are the same as defined in the formula (2)). Also, other organoaluminum compounds can be easily prepared in accordance with the same method.

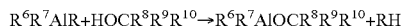

$R^6R^7AlR+HOCR^8R^9R^{10} \rightarrow R^6R^7AlOCR^8R^9R^{10}+RH$

Also, R—H byproduced in the above preparation is an inert alkane, and if it has a low boiling point, it is volatilized out of the system during the reaction step, but if it has a high boiling point, it remains in the reaction solution that is inert to the reaction.

It is preferable to carry out these reactions in an inert hydrocarbon such as hexane, heptane, octane, decane, cyclohexane, benzene, toluene, xylene or the like. Any optional reaction temperature may be employed as far as the reaction proceeds, but a preferable reaction temperature is at least 0° C., more preferably at least 20° C. The reaction mixture is heated at a temperature higher than the boiling point of a solvent used, and a reaction is often carried out under refluxing conditions of a solvent, which is a good method for completing the reaction. Any optional reaction time may be employed, but is preferably at least 1 hour, more preferably at least 2 hours. After finishing the reaction, the reaction solution is cooled, and may be supplied to the reaction with a chromium catalyst as it is, or the reaction product may be isolated by removing the catalyst, but it is preferably convenient to employ a reaction solution as it is.

The preparation method of these organoaluminum compounds and their physical and chemical properties are fully described in "Organoaluminum Compounds" by T. Mole (3rd edition, Elsevier, 1972), or the like.

In the method of the present invention, it is preferable to introduce an organoaluminum compound into the polymerization system as a co-catalyst separately from a chromium catalyst. The function of the organoaluminum compound as a co-catalyst is to reform a chromium catalyst generally hardly causing chain transfer to hydrogen so as to be capable of chain transfer to hydrogen. The details of this function mechanism are not clear, but it is considered that a part of chromium on the catalyst is converted to an active site for dissociating a hydrogen molecule by the action of these organoaluminum compounds, and the dissociated hydrogen works on a polymerization active site to cause chain transfer, thereby producing an ethylene polymer having a lower molecular weight.

In the method for producing an ethylene copolymer of the present invention, a specific organoaluminum compound is used in addition to a chromium catalyst. Among the specific organoaluminum compounds used herein, an organoaluminum compound expressed by the following formula (101) is a novel compound which is not disclosed in any known literatures.

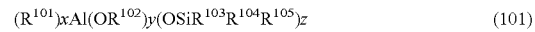

$(R^{101})_xAl(OR^{102})_y(OSiR^{103}R^{104}R^{105})_z$ \hfill (101)

(in the above formula, $R^{101}$ and $R^{102}$ may be the same or different, each represents a $C_1$-$C_{18}$ alkyl group, $R^{103}$, $R^{104}$ and $R^{105}$ may be the same or different, each represents a $C_1$-$C_{18}$ alkyl group or a $C_6$-$C_{18}$ aryl group, at least one of $R^{103}$, $R^{104}$ and $R^{105}$ is an alkyl group, and x, y and z are respectively $0.5 \leq x \leq 2$, $0.5 \leq y \leq 2$, $0.5 \leq z \leq 2$, and x+y+z=3).

Preferably, x is $1 \leq x \leq 1.5$, y is $0.5 \leq y \leq 1.5$, z is $0.5 \leq z \leq 1.5$, and x+y+z=3, and more preferably x=y=z=1.

In the particularly preferable case of x=y=z=1, the organoaluminum compound of the formula (101) can be expressed by the following formula (101').

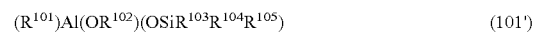

$(R^{101})Al(OR^{102})(OSiR^{103}R^{104}R^{105})$ \hfill (101')

That is, an organoaluminum compound of the formula (101) is a compound having a first atomic group such as an alkyl group, a second atomic group such as an alkoxide group and a third atomic group such as a trialkyl siloxide group, a dialkylaryl siloxide group or an alkyldiaryl siloxide group bonded to aluminum. This compound may be generally named as an alkylaluminum(alkoxide)(trialkyl siloxide), an alkylaluminum(alkoxide)(dialkylaryl siloxide) or an alkylaluminum(alkoxide)(alkyldiaryl siloxide).

Examples of the alkyl group include methyl, ethyl, n-propyl, i-propyl, n-butyl, i-butyl, sec-butyl, tert-butyl, n-pentyl, i-pentyl, neopentyl, n-hexyl, n-octyl, n-decyl, n-dodecyl, cyclohexyl, 2-methylcyclohexyl, 4-methylcyclohexyl, 2,4-dimethylcyclohexyl, 2,6-dimethylcyclohexyl, 2,4,6-trimethylcyclohexyl, exo-norbornyl, endo-norbornyl, 1-adamantyl, 2-adamantyl, benzyl, triphenylmethyl, trimethylsilylmethyl and the like.

Examples of the aryl group include phenyl, 2-methylphenyl, 3-methylphenyl, 4-methylphenyl, 2,4-dimethylphenyl, 2,6-dimethylphenyl, 2,4,6-trimethylphenyl, 2,6-di-i-propylphenyl, 2,6-di-tert-butylphenyl, 2,6-di-i-propyl-4-methylphenyl, 2,6-di-tert-butyl-4-methylphenyl, 1-naphthyl, 2-naphthyl, 1-anthryl, 2-anthryl, 9-anthryl, and the like.

Examples of $R^{101}$ include methyl, ethyl, n-butyl, i-butyl, n-hexyl, n-octyl, or the like, and among them, methyl, ethyl or i-butyl is preferable. Examples of $R^{102}$ include methyl, ethyl, n-propyl, i-propyl, n-butyl, i-butyl, sec-butyl, tert-butyl, n-pentyl, i-pentyl, neopentyl, n-hexyl, cyclohexyl, exo-norbornyl, endo-norbornyl, 1-adamantyl, 2-adamantyl, benzyl, triphenylmethyl, trimethylsilylmethyl or the like, and among them, methyl, ethyl, i-propyl, n-butyl, i-butyl, or tert-butyl is particularly preferable.

With regard to $R^{103}$, $R^{104}$ and $R^{105}$, examples of the alkyl group include methyl, ethyl, n-propyl, i-propyl, n-butyl, i-butyl, sec-butyl, tert-butyl, n-pentyl, i-pentyl, neopentyl, n-hexyl, cyclohexyl or the like, and among them, methyl or ethyl is particularly preferable. Examples of the aryl group include phenyl, 2-methylphenyl, 3-methylphenyl, 4-methylphenyl, 2,4-dimethylphenyl, 2,6-dimethylphenyl, 2,4,6-trimethylphenyl, 2,6-di-i-propylphenyl, 2,6-di-i-propyl-4-methylphenyl, 2,6-di-tert-butylphenyl, 2,6-di-tert-butyl-4-methylphenyl or the like, and among them, phenyl is particularly preferable.

In the particularly preferable case of x=y=z=1, examples of the organoaluminum compound of the formula (101) include methylaluminum(methoxide)(trimethyl siloxide), methylaluminum(methoxide)(triethyl siloxide), methylaluminum(methoxide)(ethyldimethyl siloxide), methylaluminum(methoxide)(i-butyldimethyl siloxide), methylaluminum(methoxide)(phenyldimethyl siloxide), methylaluminum(methoxide)(phenylethylmethyl siloxide), methylaluminum(methoxide)(phenyl-i-butylmethyl siloxide), methylaluminum(methoxide)(methyldiphenyl siloxide), methylaluminum(methoxide)(ethyldiphenyl siloxide), methylaluminum(methoxide)(i-butyldiphenyl siloxide), methylaluminum(ethoxide)(trimethyl siloxide), methylaluminum(ethoxide)(triethyl siloxide), methylaluminum(ethoxide)(ethyldimethyl siloxide), methylaluminum(ethoxide)(i-butyldimethyl siloxide), methylaluminum(ethoxide)(phenyldimethyl siloxide), methylaluminum(ethoxide)(phenylethylmethyl siloxide), methylaluminum(ethoxide)(phenyl-i-butylmethyl siloxide), methylaluminum(ethoxide)(methyldiphenyl siloxide), methylaluminum(ethoxide)(ethyldiphenyl siloxide), methylaluminum(ethoxide)(i-butyldiphenyl siloxide), methylaluminum(i-propoxide)(trimethyl siloxide), methylaluminum(i-propoxide)(triethyl siloxide), methylaluminum(i-propoxide)(ethyldimethyl siloxide), methylaluminum(i-propoxide)(i-butyldimethyl siloxide), methylaluminum(i-propoxide)(phenyldimethyl siloxide), methylaluminum(i-propoxide)(phenylethylmethyl siloxide), methylaluminum(i-propoxide)(phenyl-i-butylmethyl siloxide), methylaluminum(i-propoxide)(methyldimethyl siloxide), methylaluminum(i-propoxide)(ethyldiphenyl siloxide), methylaluminum(i-propoxide)(i-butyldiphenyl siloxide), methylaluminum(n-butoxide)(trimethyl siloxide), methylaluminum(n-butoxide)(triethyl siloxide), methylaluminum(n-butoxide)(ethyldimethyl siloxide), methylaluminum(n-butoxide)(i-butyldimethyl siloxide), methylaluminum(n-butoxide)(phenyldimethyl siloxide), methylaluminum(n-butoxide)(phenylethylmethyl siloxide), methylaluminum(n-butoxide)(phenyl-i-butylmethyl siloxide), methylaluminum(n-butoxide)(methyldiphenyl siloxide), methylaluminum(n-butoxide)(ethyldiphenyl siloxide), methylaluminum(n-butoxide)(i-butyldipnehyl siloxide), methylaluminum(i-butoxide)(trimethyl siloxide), methylaluminum(i-butoxide)(triethyl siloxide), methylaluminum(i-butoxide)(ethyldimethyl siloxide), methylaluminum(i-butoxide)(i-butyldimethyl siloxide), methylaluminum(i-butoxide)(phenyldimethyl siloxide), methylaluminum(i-butoxide)(phenylethylmethyl siloxide), methylaluminum(i-butoxide)(phenyl-i-butylmethyl siloxide), methylaluminum(i-butoxide)(methyldiphenyl siloxide), methylaluminum(i-butoxide)(ethyldiphenyl siloxide), methylaluminum(i-butoxide)(i-butyldipnehyl siloxide), methylaluminum(tert-butoxide)(trimethyl siloxide), methylaluminum(tert-butoxide)(triethyl siloxide), methylaluminum(tert-butoxide)(ethyldimethyl siloxide), methylaluminum(tert-butoxide)(i-butyldimethyl siloxide), methylaluminum(tert-butoxide)(phenyldimethyl siloxide), methylaluminum(tert-butoxide)(phenylethylmethyl siloxide), methylaluminum(tert-butoxide)(phenyl-i-butylmethyl siloxide), methylaluminum(tert-butoxide)(methyldiphenyl siloxide), methylaluminum(tert-butoxide)(ethyldiphenyl siloxide), methylaluminum(tert-butoxide)(i-butyldiphenyl siloxide), ethylaluminum(methoxide)(trimethyl siloxide), ethylaluminum(methoxide)(triethyl siloxide), ethylaluminum(methoxide)(ethyldimethyl siloxide), ethylaluminum(methoxide)(i-butyldimethyl siloxide), ethylaluminum(methoxide)(phenyldimethyl siloxide), ethylaluminum(methoxide)(phenylethylmethyl siloxide), ethylaluminum(methoxide)(phenyl-i-butylmethyl siloxide), ethylaluminum(methoxide)(methyldiphenyl siloxide), ethylaluminum(methoxide)(ethyldiphenyl siloxide), ethylaluminum(methoxide)(i-butyldiphenyl siloxide), ethylaluminum(ethoxide)(trimethyl siloxide), ethylaluminum(ethoxide)(triethyl siloxide), ethylaluminum(ethoxide)(ethyldimethyl siloxide), ethylaluminum(ethoxide)(i-butyldimethyl siloxide), ethylaluminum(ethoxide)(phenyldimethyl siloxide), ethylaluminum(ethoxide)(phenylethylmethyl siloxide), ethylaluminum(ethoxide)(phenyl-i-butylmethyl siloxide), ethylaluminum(ethoxide)(methyldiphenyl siloxide), ethylaluminum(ethoxide)(ethyldiphenyl siloxide), ethylaluminum(ethoxide)(i-butyldiphenyl siloxide), ethylaluminum(i-propoxide)(trimethyl siloxide), ethylaluminum(i-propoxide)(triethyl siloxide), ethylaluminum(i-propoxide)(ethyldimethyl siloxide), ethylaluminum(i-propoxide)(i-butyldimethyl siloxide), ethylaluminum(i-propoxide)(phenyldimethyl siloxide), ethylaluminum(i-propoxide)(phenylethylmethyl siloxide), ethylaluminum(i-propoxide)(phenyl-i-butylmethyl siloxide), ethylaluminum(i-propoxide)(methyldiphenyl siloxide), ethylaluminum(i-propoxide)(ethyldiphenyl siloxide), ethylaluminum(i-propoxide)(i-butyldiphenyl siloxide), ethylaluminum(n-butoxide)(trimethyl siloxide), ethylaluminum(n-butoxide)(triethyl siloxide), ethylaluminum(n-butoxide)(ethyldimethyl siloxide), ethylaluminum(n-butoxide)(i-butyldimethyl siloxide), ethylaluminum(n-butoxide)(phenyldimethyl siloxide), ethylaluminum(n-butoxide)(phenylethylmethyl siloxide), ethylaluminum(n-butoxide)(phenyl-i-butylmethyl siloxide), ethylaluminum(n-butoxide)(methyldiphenyl siloxide), ethylaluminum(n-butoxide)(ethyldiphenyl siloxide), ethylaluminum(n-butoxide)(i-butyldipnehyl siloxide), ethylaluminum(i-butoxide)(trimethyl siloxide), ethylaluminum(i-butoxide)(triethyl siloxide), ethylaluminum(i-butoxide)(ethyldimethyl siloxide), ethylaluminum(i-butoxide)(i-butyldimethyl siloxide), ethylaluminum(i-butoxide)(phenyldimethyl siloxide), ethylaluminum(i-butoxide)(phenylethylmethyl siloxide), ethylaluminum(i-butoxide)(phenyl-i-butylmethyl siloxide), ethylaluminum(i-butoxide)(methyldiphenyl siloxide), ethylaluminum(i-butoxide)(ethyldiphenyl siloxide), ethylaluminum(i-butoxide)(i-butyldiphenyl siloxide), ethylaluminum(tert-butoxide)(trimethyl siloxide), ethylaluminum(tert-butoxide)(triethyl siloxide), ethylaluminum(tert-butoxide)(ethyldimethyl siloxide), ethylaluminum(tert-butoxide)(i-butyldimethyl siloxide), ethylaluminum(tert-butoxide)(phenyldimethyl siloxide), ethylaluminum(tert-butoxide)(phenylethylmethyl siloxide), ethylaluminum(tert-butoxide)(phenyl-i-butylmethyl siloxide), ethylaluminum(tert-butoxide)(methyldiphenyl siloxide), ethylaluminum(tert-butoxide)(ethyldiphenyl siloxide), ethylaluminum(tert-butoxide)(i-butyldiphenyl siloxide), n-butylaluminum(methoxide)(trimethyl siloxide), n-butylaluminum(methoxide)(triethyl siloxide), n-butylaluminum(methoxide)(ethyldimethyl siloxide), n-butylaluminum(methoxide)(i-butyldimethyl siloxide), n-butylaluminum(methoxide)(phenyldimethyl siloxide), n-butylaluminum(methoxide)(phenylethylmethyl siloxide), n-butylaluminum(methoxide)(phenyl-i-butylmethyl siloxide), n-butylaluminum(methoxide)(methyldiphenyl siloxide), n-butylaluminum(methoxide)(ethyldiphenyl siloxide), n-butylaluminum(methoxide)(i-butyldipnehyl siloxide), n-butylaluminum(ethoxide)(trimethyl siloxide), n-butylaluminum(ethoxide)(triethyl siloxide), n-butylaluminum(ethoxide)(ethyldimethyl siloxide), n-butylaluminum(ethoxide)(i-butyldimethyl siloxide), n-butylaluminum(ethoxide)(phenyldimethyl siloxide), n-butylaluminum(ethoxide)(phenylethylmethyl siloxide), n-butylaluminum(ethoxide)(phenyl-i-butylmethyl siloxide), n-butylaluminum(ethoxide)(methyldiphenyl siloxide), n-butylaluminum(ethoxide)(ethyldiphenyl siloxide), n-butylaluminum (ethoxide)(i-butyldiphenyl siloxide), n-butylaluminum(i-propoxide)(trimethyl siloxide), n-butylaluminum(i-propoxide)(triethyl siloxide), n-butylaluminum(i-propoxide)(ethyldimethyl siloxide), n-butylaluminum(i-propoxide)(i-butyldimethyl siloxide), n-butylaluminum(i-propoxide)(phenyldimethyl siloxide), n-butylaluminum(i-propoxide)(phenylethylmethyl siloxide), n-butylaluminum(i-propoxide)(phenyl-i-butylmethyl siloxide), n-butylaluminum(i-propoxide)(methyldiphenyl siloxide), n-butylaluminum(i-propoxide)(ethyldiphenyl siloxide), n-butylaluminum(i-propoxide)(i-butyldiphenyl siloxide), n-butylaluminum(n-butoxide)(trimethyl siloxide), n-butylaluminum(n-butoxide)(triethyl siloxide), n-butylaluminum(n-butoxide)(ethyldimethyl siloxide), n-butylaluminum(n-butoxide)(i-butyldimethyl siloxide), n-butylaluminum(n-butoxide)(phenyldimethyl siloxide), n-butylaluminum(n-butoxide)(phenylethylmethyl siloxide), n-butylaluminum(n-butoxide)(phenyl-i-butylmethyl siloxide), n-butylaluminum(n-butoxide)(methyldiphenyl siloxide), n-butylaluminum(n-butoxide)(ethyldiphenyl siloxide), n-butylaluminum(n-butoxide)(i-butyldiphenyl siloxide), n-butylaluminum(i-butoxide)(trimethyl siloxide), n-butylaluminum(i-butoxide)(triethyl siloxide), n-butylaluminum(i-butoxide)(ethyldimethyl siloxide), n-butylaluminum(i-butoxide)(i-butyldimethyl siloxide), n-butylaluminum(i-butoxide)(phenyldimethyl siloxide), n-butylaluminum(i-butoxide)(phenylethylmethyl siloxide), n-butylaluminum(i-butoxide)(phenyl-i-butylmethyl siloxide), n-butylaluminum(i-butoxide)(methyldiphenyl siloxide), n-butylaluminum(i-butoxide)(ethyldiphenyl siloxide), n-butylaluminum(i-butoxide)(i-butyldiphenyl siloxide), n-butylaluminum(tert-butoxide)(trimethyl siloxide), n-butylaluminum(tert-butoxide)(triethyl siloxide), n-butylaluminum(tert-butoxide)(ethyldimethyl siloxide), n-butylaluminum(tert-butoxide)(i-butyldimethyl siloxide), n-butylaluminum(tert-butoxide)(phenyldimethyl siloxide), n-butylaluminum(tert-butoxide)(phenylethylmethyl siloxide), n-butylaluminum(tert-butoxide)(phenyl-i-butylmethyl siloxide), n-butylaluminum(tert-butoxide)(methyldiphenyl siloxide), n-butylaluminum(tert-butoxide)(ethyldiphenyl siloxide), n-butylaluminum(tert-butoxide)(i-butyldiphenyl siloxide), i-butylaluminum(methoxide)(trimethyl siloxide), i-butylaluminum(methoxide)(triethyl siloxide), i-butylaluminum(methoxide)(ethyldimethyl siloxide), i-butylaluminum(methoxide)(i-butyldimethyl siloxide), i-butylaluminum(methoxide)(phenyldimethyl siloxide), i-butylaluminum(methoxide)(phenylethylmethyl siloxide), i-butylaluminum(methoxide)(phenyl-i-butylmethyl siloxide), i-butylaluminum(methoxide)(methyldiphenyl siloxide), i-butylaluminum(methoxide)(ethyldiphenyl siloxide), i-butylaluminum(methoxide)(i-butyldiphenyl siloxide), i-butylaluminum(ethoxide)(trimethyl siloxide), i-butylaluminum(ethoxide)(triethyl siloxide), i-butylaluminum(ethoxide)(ethyldimethyl siloxide), i-butylaluminum(ethoxide)(i-butyldimethyl siloxide), i-butylaluminum(ethoxide)(phenyldimethyl siloxide), i-butylaluminum(ethoxide)(phenylethylmethyl siloxide), i-butylaluminum(ethoxide)(phenyl-i-butylmethyl siloxide), i-butylaluminum(ethoxide)(methyldiphenyl siloxide), i-butylaluminum(ethoxide)(ethyldiphenyl siloxide), i-butylaluminum(ethoxide)(i-butyldiphenyl siloxide), i-butylaluminum(i-propoxide)(trimethyl siloxide), i-butylaluminum(i-propoxide)(triethyl siloxide), i-butylaluminum(i-propoxide)(ethyldimethyl siloxide), i-butylaluminum(i-propoxide)(i-butyldimethyl siloxide), i-butylaluminum(i-propoxide)(phenyldimethyl siloxide), i-butylaluminum(i-propoxide)(phenylethylmethyl siloxide), i-butylaluminum(i-propoxide)(phenyl-i-butylmethyl siloxide), i-butylaluminum(i-propoxide)(methyldiphenyl siloxide), i-butylaluminum(i-propoxide)(ethyldiphenyl siloxide), i-butylaluminum(i-propoxide)(i-butyldiphenyl siloxide), i-butylaluminum(n-butoxide)(trimethyl siloxide), i-butylaluminum(n-butoxide)(triethyl siloxide), i-butylaluminum(n-butoxide)(ethyldimethyl siloxide), i-butylaluminum(n-butoxide)(i-butyldimethyl siloxide), i-butylaluminum(n-butoxide)(phenyldimethyl siloxide), i-butylaluminum(n-butoxide)(phenylethylmethyl siloxide), i-butylaluminum(n-butoxide)(phenyl-1-butylmethyl siloxide), i-butylaluminum(n-butoxide)(methyldiphenyl siloxide), i-butylaluminum(n-butoxide)(ethyldiphenyl siloxide), i-butylaluminum (n-butoxide)(i-butyldiphenyl siloxide), i-butylaluminum(i-butoxide)(trimethyl siloxide), i-butylaluminum(i-butoxide)(triethyl siloxide), i-butylaluminum(i-butoxide)(ethyldimethyl siloxide), i-butylaluminum(i-butoxide)(i-butyldimethyl siloxide), i-butylaluminum(i-butoxide)(phenyldimethyl siloxide), i-butylaluminum(i-butoxide)(phenylethylmethyl siloxide), i-butylaluminum(i-butoxide)(phenyl-i-butylmethyl siloxide), i-butylaluminum(i-butoxide)(methyldiphenyl siloxide), i-butylaluminum(i-butoxide)(ethyldiphenyl siloxide), i-butylaluminum(i-butoxide)(i-butyldiphenyl siloxide), i-butylaluminum(tert-butoxide)(trimethyl siloxide), i-butylaluminum(tert-butoxide)(triethyl siloxide), i-butylaluminum(tert-butoxide)(ethyldimethyl siloxide), i-butylaluminum(tert-butoxide)(i-butyldimethyl siloxide), i-butylaluminum(tert-butoxide)(phenyldimethyl siloxide), i-butylaluminum(tert-butoxide)(phenylethylmethyl siloxide), i-butylaluminum(tert-butoxide)(phenyl-i-butylmethyl siloxide), i-butylaluminum (tert-butoxide)(methyldiphenyl siloxide), i-butylaluminum (tert-butoxide)(ethyldiphenyl siloxide), i-butylaluminum (tert-butoxide)(i-butyldiphenyl siloxide), n-hexylaluminum(methoxide)(trimethyl siloxide), n-hexylaluminum(methoxide)(triethyl siloxide), n-hexylaluminum(methoxide)(ethyldimethyl siloxide), n-hexylaluminum(methoxide)(i-butyldimethyl siloxide), n-hexylaluminum(methoxide)(phenyldimethyl siloxide), n-hexylaluminum(methoxide)(phenylethylmethyl siloxide), n-hexylaluminum(methoxide)(phenyl-i-butylmethyl siloxide), n-hexylaluminum(methoxide)(methyldiphenyl siloxide), n-hexylaluminum(methoxide)(ethyldiphenyl siloxide), n-hexylaluminum(methoxide)(i-butyldiphenyl siloxide), n-hexylaluminum(ethoxide)(trimethyl siloxide), n-hexylaluminum(ethoxide)(triethyl siloxide), n-hexylaluminum(ethoxide)(ethyldimethyl siloxide), n-hexylaluminum(ethoxide)(i-butyldimethyl siloxide), n-hexylaluminum(ethoxide)(phenyldimethyl siloxide), n-hexylaluminum(ethoxide)(phenylethylmethyl siloxide), n-hexylaluminum(ethoxide)(phenyl-i-butylmethyl siloxide), n-hexylaluminum(ethoxide)(methyldiphenyl siloxide), n-hexylaluminum(ethoxide)(ethyldiphenyl siloxide), n-hexylaluminum(ethoxide)(i-butyldiphenyl siloxide), n-hexylaluminum(i-propoxide)(trimethyl siloxide), n-hexylaluminum(i-propoxide)(triethyl siloxide), n-hexylaluminum(i-propoxide)(ethyldimethyl siloxide), n-hexylaluminum(i-propoxide)(i-butyldimethyl siloxide), n-hexylaluminum(i-propoxide)(phenyldimethyl siloxide), n-hexylaluminum(i-propoxide)(phenylethylmethyl siloxide), n-hexylaluminum(i-propoxide)(phenyl-i-butylmethyl siloxide), n-hexylaluminum(i-propoxide)(methyldiphenyl siloxide), n-hexylaluminum(i-propoxide)(ethyldiphenyl siloxide), n-hexylaluminum(i-propoxide)(i-butyldiphenyl siloxide), n-hexylaluminum(n-butoxide)(trimethyl siloxide), n-hexylaluminum(n-butoxide)(triethyl siloxide), n-hexylaluminum(n-butoxide)(ethyldimethyl siloxide), n-hexylaluminum(n-butoxide)(i-butyldimethyl siloxide), n-hexylaluminum(n-butoxide)(phenyldimethyl siloxide), n-hexylaluminum(n-butoxide)(phenylethylmethyl siloxide), n-hexylaluminum(n-butoxide)(phenyl-i-butylmethyl siloxide), n-hexylaluminum(n-butoxide)(methyldiphenyl siloxide), n-hexylaluminum(n-butoxide)(ethyldiphenyl siloxide), n-hexylaluminum(n-butoxide)(i-butyldiphenyl siloxide), n-hexylaluminum(i-butoxide)(trimethyl siloxide), n-hexylaluminum(i-butoxide)(triethyl siloxide), n-hexylaluminum(i-butoxide)(ethyldimethyl siloxide), n-hexylaluminum(i-butoxide)(i-butyldimethyl siloxide), n-hexylaluminum(i-butoxide)(phenyldimethyl siloxide), n-hexylaluminum(i-butoxide)(phenylethylmethyl siloxide), n-hexylaluminum(i-butoxide)(phenyl-i-butylmethyl siloxide), n-hexylaluminum(i-butoxide)(methyldiphenyl siloxide), n-hexylaluminum(i-butoxide)(ethyldiphenyl siloxide), n-hexylaluminum(i-butoxide)(i-butyldiphenyl siloxide), n-hexylaluminum(tert-butoxide)(trimethyl siloxide), n-hexylaluminum(tert-butoxide)(triethyl siloxide), n-hexylaluminum(tert-butoxide)(ethyldimethyl siloxide), n-hexylaluminum(tert-butoxide)(i-butyldimethyl siloxide), n-hexylaluminum(tert-butoxide)(phenyldimethyl siloxide), n-hexylaluminum(tert-butoxide)(phenylethylmethyl siloxide), n-hexylaluminum(tert-butoxide)(phenyl-i-butylmethyl siloxide), n-hexylaluminum(tert-butoxide)(methyldiphenyl siloxide), n-hexylaluminum(tert-butoxide)(ethyldiphenyl siloxide), n-hexylaluminum(tert-butoxide)(i-butyldiphenyl siloxide), n-octylaluminum(methoxide)(trimethyl siloxide), n-octylaluminum(methoxide)(triethyl siloxide), n-octylaluminum(methoxide)(ethyldimethyl siloxide), n-octylaluminum(methoxide)(i-butyldimethyl siloxide), n-octylaluminum(methoxide)(phenyldimethyl siloxide), n-octylaluminum(methoxide)(phenylethylmethyl siloxide), n-octylaluminum(methoxide)(phenyl-i-butylmethyl siloxide), n-octylaluminum(methoxide)(methyldiphenyl siloxide), n-octylaluminum(methoxide)(ethyldiphenyl siloxide), n-octylaluminum(methoxide)(i-butyldiphenyl siloxide), n-octylaluminum(ethoxide)(trimethyl siloxide), n-octylaluminum(ethoxide)(triethyl siloxide), n-octylaluminum(ethoxide)(ethyldimethyl siloxide), n-octylaluminum(ethoxide)(i-butyldimethyl siloxide), n-octylaluminum(ethoxide)(phenyldimethyl siloxide), n-octylaluminum(ethoxide)(phenylethylmethyl siloxide), n-octylaluminum(ethoxide)(phenyl-i-butylmethyl siloxide), n-octylaluminum(ethoxide)(methyldiphenyl siloxide), n-octylaluminum(ethoxide)(ethyldiphenyl siloxide), n-octylaluminum(ethoxide)(i-butyldiphenyl siloxide), n-octylaluminum(i-propoxide)(trimethyl siloxide), n-octylaluminum(i-propoxide)(triethyl siloxide), n-octylaluminum(i-propoxide)(ethyldimethyl siloxide), n-octylaluminum(i-propoxide)(i-butyldimethyl siloxide), n-octylaluminum(i-propoxide)(phenyldimethyl siloxide), n-octylaluminum(i-propoxide)(phenylethylmethyl siloxide), n-octylaluminum(i-propoxide)(phenyl-i-butylmethyl siloxide), n-octylaluminum(i-propoxide)(methyldiphenyl siloxide), n-octylaluminum(i-propoxide)(ethyldiphenyl siloxide), n-octylaluminum(i-propoxide)(i-butyldiphenyl siloxide), n-octylaluminum(n-butoxide)(trimethyl siloxide), n-octylaluminum(n-butoxide)(triethyl siloxide), n-octylaluminum(n-butoxide)(ethyldimethyl siloxide), n-octylaluminum(n-butoxide)(i-butyldimethyl siloxide), n-octylaluminum(n-butoxide)(phenyldimethyl siloxide), n-octylaluminum(n-butoxide)(phenylethylmethyl siloxide), n-octylaluminum(n-butoxide)(phenyl-i-butylmethyl siloxide), n-octylaluminum(n-butoxide)(methyldiphenyl siloxide), n-octylaluminum(n-butoxide)(ethyldiphenyl siloxide), n-octylaluminum(n-butoxide)(i-butyldiphenyl siloxide), n-octylaluminum(i-butoxide)(trimethyl siloxide), n-octylaluminum(i-butoxide)(triethyl siloxide), n-octylaluminum(i-butoxide)(ethyldimethyl siloxide), n-octylaluminum(i-butoxide)(i-butyldimethyl siloxide), n-octylaluminum(i-butoxide)(phenyldimethyl siloxide), n-octylaluminum(i-butoxide)(phenylethylmethyl siloxide) n-octylaluminum(i-butoxide)(phenyl-i-butylmethyl siloxide), n-octylaluminum(i-butoxide)(methyldiphenyl siloxide), n-octylaluminum(i-butoxide)(ethyldiphenyl siloxide), n-octylaluminum(i-butoxide)(i-butyldiphenyl siloxide), n-octylaluminum(tert-butoxide)(trimethyl siloxide), n-octylaluminum(tert-butoxide)(triethyl siloxide), n-octylaluminum(tert-butoxide)(ethyldimethyl siloxide), n-octylaluminum(tert-butoxide)(i-butyldimethyl siloxide), n-octylaluminum(tert-butoxide)(phenyldimethyl siloxide), n-octylaluminum(tert-butoxide)(phenylethylmethyl siloxide), n-octylaluminum(tert-butoxide)(phenyl-i-butylmethyl siloxide), n-octylaluminum(tert-butoxide)(methyldiphenyl siloxide), n-octylaluminum(tert-butoxide)(ethyldiphenyl siloxide), n-octylaluminum(tert-butoxide)(i-butyldiphenyl siloxide) or the like.

(Method for Producing Organoaluminum Compound)

The organoaluminum compound of the formula (101) can be prepared in accordance with the following processes (1) to (7).

(1) Process for Reacting Trialkylaluminum with Alcohol and Silanol

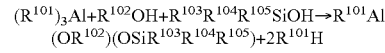

$(R^{101})_3Al + R^{102}OH + R^{103}R^{104}R^{105}SiOH \rightarrow R^{101}Al(OR^{102})(OSiR^{103}R^{104}R^{105}) + 2R^{101}H$ In the above reaction formula, $R^{101}$ to $R^{105}$, x, y and z are the same as defined in the formula (101) (hereinafter, these definitions are the same in the present paragraph (Method for producing organoaluminum compound)). The above process (1) is used preferably for producing a preferable compound of the formula (101) wherein x=y=z=1.

Examples of a trialkylaluminum expressed by $(R^{101})_3Al$ include trimethylaluminum, triethylaluminum, tri-n-butylaluminum, tri-i-butylaluminum, tri-n-hexylaluminum, tri-n-octylaluminum or the like, and among them, trimethylaluminum, triethylaluminum or tri-i-butylaluminum is preferable.

Examples of an alcohol expressed by $R^{102}OH$ include methanol, ethanol, n-propanol, i-propanol, n-butanol, i-butanol, sec-butanol, tert-butanol, n-pentanol, i-pentanol, neopentyl alcohol, n-hexanol, cyclohexanol, exo-norbornyl alcohol, endo-norbornyl alcohol, 1-adamantyl alcohol, 2-adamantyl alcohol, benzyl alcohol, triphenylmethanol, trimethylsilylmethanol or the like, and among them, methanol, ethanol, i-propanol, n-butanol, i-butanol or tert-butanol is preferable.

Examples of a silanol expressed by $R^{103}R^{104}R^{105}SiOH$ include trimethylsilanol, triethylsilanol, tri-n-propylsilanol, tri-i-propylsilanol, tri-n-butylsilanol, ethyldimethylsilanol, i-butyldimethylsilanol, phenyldimethylsilanol, phenylethylmethylsilanol, phenyl-i-butylmethylsilanol, methyldiphenylsilanol, ethyldiphenylsilanol, i-butyldiphenylsilanol or the like, and among them, trimethylsilanol or triethylsilanol is preferable.

According to this process, a trialkylaluminum $(R^{101})_3Al$, an alcohol $R^{102}OH$ and a silanol $R^{103}R^{104}R^{105}SiOH$ may be reacted, but it is usual to react first a trialkylaluminum $(R^{101})_3Al$ with an alcohol $R^{102}OH$ and then to react a silanol $R^{103}R^{104}R^{105}SiOH$, or preferably to react first a trialkylaluminum $(R^{101})_3Al$ with a silanol $R^{103}R^{104}R^{105}SiOH$ and then to react an alcohol $R^{102}OH$.

(2) Process for Reacting Dialkylaluminum Alkoxide with Silanol

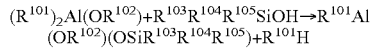
$(R^{101})_2Al(OR^{102})+R^{103}R^{104}R^{105}SiOH \rightarrow R^{101}Al(OR^{102})(OSiR^{103}R^{104}R^{105})+R^{101}H$ Examples of a dialkylaluminum alkoxide expressed by $(R^{101})_2Al(OR^{102})$ include dimethylaluminum methoxide, dimethylaluminum ethoxide, dimethylaluminum i-propoxide, dimethylaluminum n-butoxide, dimethylaluminum i-butoxide, dimethylaluminum tert-butoxide, diethylaluminum methoxide, diethylaluminum ethoxide, diethylaluminum i-propoxide, diethylaluminum n-butoxide, diethylaluminum i-butoxide, diethylaluminum tert-butoxide, di-n-butylaluminum methoxide, di-n-butylaluminum ethoxide, di-n-butylaluminum i-propoxide, di-n-butylaluminum n-butoxide, di-n-butylaluminum i-butoxide, di-n-butylaluminum tert-butoxide, di-i-butylaluminum methoxide, di-i-butylaluminum ethoxide, di-i-butylaluminum i-propoxide, di-i-butylaluminum n-butoxide, di-i-butylaluminum i-butoxide, di-i-butylaluminum tert-butoxide, di-n-hexylaluminum methoxide, di-n-hexylaluminum ethoxide, di-n-hexylaluminum i-propoxide, di-n-hexylaluminum n-butoxide, di-n-hexylaluminum i-butoxide, di-n-hexylaluminum tert-butoxide, di-n-octylaluminum methoxide, di-n-octylaluminum ethoxide, di-n-octylaluminum i-propoxide, di-n-octylaluminum n-butoxide, di-n-octylaluminum i-butoxide, di-n-octylaluminum tert-butoxide, or the like.

Examples of a silanol expressed by $R^{103}R^{104}R^{105}SiOH$ include those illustrated in the above paragraph (1). According to this process, a dialkylaluminum alkoxide $(R^{101})_2Al(OR^{102})$ is simply reacted with a silanol $R^{103}R^{104}R^{105}SiOH$. In this process, a dialkylaluminum alkoxide is used in an amount of stoichiometrically up to two times to a silanol, and not only in the case of x=y=z=1 but also a case of other than 1 is preferably used.

(3) Process for Reacting Dialkylaluminum Halide with Metal Alkoxide and Silanol

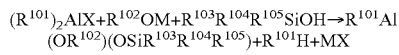
$(R^{101})_2AlX+R^{102}OM+R^{103}R^{104}R^{105}SiOH \rightarrow R^{101}Al(OR^{102})(OSiR^{103}R^{104}R^{105})+R^{101}H+MX$ This process is preferably employed for producing a preferable compound of the formula (101) wherein x=y=z=1.

X in $(R^{101})_2AlX$ is fluorine, chlorine, bromine or iodine, and chlorine is particularly preferable. Examples of a dialkylaluminum halide expressed by $(R^{101})_2AlX$ include dimethylaluminum chloride, diethylaluminum chloride, di-n-propylaluminum chloride, di-n-butylaluminum chloride, di-i-butylaluminum chloride or the like. M in $R^{102}OM$ is an alkali metal, and lithium, sodium or potassium is particularly preferable. Examples of a metal alkoxide expressed by $R^{102}OM$ include an alkali metal salt of an alcohol illustrated in the above paragraph (1), and a lithium salt, a sodium salt or a potassium salt is particularly preferable. Examples of a silanol expressed by $R^{103}R^{104}R^{105}SiOH$ include those illustrated in the above paragraph (1).

According to this process, it is preferable to react first a dialkylaluminum halide $(R^{101})_2AlX$ with a metal alkoxide $R^{102}OM$ and then to react a silanol $R^{103}R^{104}R^{105}SiOH$, or to react first a dialkylaluminum halide $(R^{101})_2AlX$ with a silanol $R^{103}R^{104}R^{105}SiOH$ and then to react a metal alkoxide $R^{102}OM$.

(4) Process for Reacting Dialkylaluminum Halide with Metal Siloxide and Alcohol

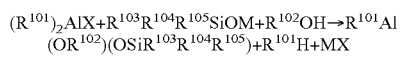
$(R^{101})_2AlX+R^{103}R^{104}R^{105}SiOM+R^{102}OH \rightarrow R^{101}Al(OR^{102})(OSiR^{103}R^{104}R^{105})+R^{101}H+MX$ This process is preferably employed for producing a preferable compound of the formula (101) wherein x=y=z=1.

M in $R^{103}R^{104}R^{105}SiOM$ is an alkali metal, and lithium, sodium or potassium is particularly preferable. Examples of a metal siloxide expressed by $R^{103}R^{104}R^{105}SiOM$ include an alkali metal of a silanol illustrated in the above paragraph (1), and a lithium salt, a sodium salt or a potassium salt is particularly preferable. According to this process, it is preferable to react first a dialkylaluminum halide $(R^{101})_2AlX$ with a metal siloxide $R^{103}R^{104}R^{105}SiOM$ and then to react an alcohol $R^{102}OH$, or to react first a dialkylaluminum halide $(R^{101})_2AlX$ with an alcohol $R^{102}OH$ and then to react a metal siloxide $R^{103}R^{104}R^{105}SiOM$.

(5) Process for Reacting Alkylaluminum Dihalide with Metal Alkoxide and Metal Siloxide

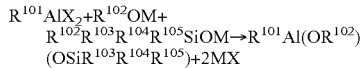
$R^{101}AlX_2+R^{102}OM+R^{103}R^{104}R^{105}SiOM \rightarrow R^{101}Al(OR^{102})(OSiR^{103}R^{104}R^{105})+2MX$ This process is preferably employed for producing a preferable compound of the formula (101) wherein x=y=z=1.

X in $R^{101}Al(X)_2$ include fluorine, chlorine, bromine or iodine, and chlorine is particularly preferable. Examples of an alkylaluminum dihalide expressed by $R^{101}Al(X)_2$ include methylaluminum dichloride, ethylaluminum dichloride, n-propylaluminum dichloride, n-butylaluminum dichloride, i-butylaluminum dichloride or the like. M in $R^{102}OM$ is an alkali metal, and lithium, sodium or potassium is particularly preferable. Examples of a metal alkoxide expressed by $R^{102}OM$ include an alkali metal salt of an alcohol illustrated in the above paragraph (1), and a lithium salt, a sodium salt or a potassium salt is particularly preferable. Examples of a metal siloxide expressed by $R^{103}R^{104}R^{105}SiOM$ include an alkali metal salt of a silanol illustrated in the above paragraph (1), and a lithium salt, a sodium salt or a potassium salt is particularly preferable.

According to this process, it is preferable to react first an alkyl aluminum dihalide $R^{101}AlX_2$ with a metal alkoxide $R^{102}OM$ and then to react a metal siloxide $R^{103}R^{104}R^{105}SiOM$, or to react first an alkyl aluminum dihalide $R^{101}AlX_2$ with a metal siloxide $R^{103}R^{104}R^{105}SiOM$ and then to react a metal alkoxide $R^{102}OM$.

(6) Process for Reacting Dialkylaluminum Alkoxide with Polysiloxane

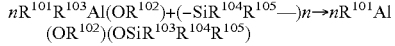
$nR^{101}R^{103}Al(OR^{102})+(-SiR^{104}R^{105}-)n \rightarrow nR^{101}Al(OR^{102})(OSiR^{103}R^{104}R^{105})$ Examples of a dialkylaluminum alkoxide expressed by $R^{101}R^{103}Al(OR^{102})$ include those illustrated in the above paragraph (2).

$(-SiR^{104}R^{105}O-)_n$ represents a poly(dialkylsiloxane), examples of which include poly(dimethylsiloxane), poly(methylethylsiloxane), poly(diethylsiloxane), poly(phenylmethylsiloxane), poly(phenylethylsiloxane), poly(diphenylsiloxane) or the like, and poly(dimethylsiloxane) or poly(diphenylsiloxane) is particularly preferable. They may be any of a straight chain-like structure and a cyclic structure, but a cyclic structure is preferable in view of purity of a product. n is at least 2, preferably at least 4. These polysiloxanes may have various viscosities, but it is particularly preferable to use a polysiloxane having a viscosity at 30° C. of from 10 to 1,000 centistokes.

According to this process, a dialkylaluminum alkoxide $R^{101}R^{103}Al(OR^{102})$ is simply reacted with a poly(dialkylsiloxane) $(-SiR^{104}R^{105}O-)_n$. Also, in this process, a dialkylaluminum alkoxide is used in an amount of stoichiometrically up to 2n times to a polysiloxane, and this process is preferably usable not only in the case of x=y=z=1 but also in a case of other than 1.

(7) Process for Reacting Trialkylaluminum with Polysiloxane and Alcohol

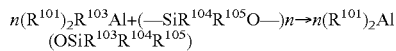

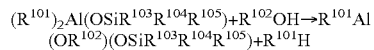

This process is preferably employed for producing a preferable compound of the formula (101) wherein x=y=z=1.

Examples of a trialkylaluminum $(R^{101})_2R^{103}Al$ and an alcohol $R^{102}OH$ include those illustrated in the above paragraph (1), and examples of a polysiloxane $(-SiR^{104}R^{105}O-)_n$ include those illustrated in the above paragraph (6). According to this process, a trialkylaluminum $(R^{101})_2R^{103}Al$ is reacted with a polysiloxane $(-SiR^{104}R^{105}O-)_n$ to obtain a dialkylaluminum siloxide $(R^{101})_2Al(OSiR^{103}R^{104}R^{105})$, which is then reacted with an alcohol $R^{102}OH$.

These processes (1) to (7) are preferably carried out in an inert hydrocarbon such as hexane, heptane, octane, decane, cyclohexane, benzene, toluene, xylene or the like. Any optional reaction temperature may be employed as far as the reaction proceeds, but a preferable reaction temperature is at least 0° C., more preferably at least 20° C. The reaction mixture is heated at a temperature higher than a boiling point of a solvent used, and a reaction is often carried out under refluxing conditions of a solvent, which is a good method for completing the reaction. Any optional reaction time may be employed, but is preferably at least 1 hour, more preferably at least 2 hours. After finishing the reaction, the reaction solution is cooled, and may be used as it is, or may be used after removing the solvent and isolating a reaction product, but it is convenient and preferable to use the reaction solution as it is. A byproduct $(R^{101}H)$ in the above process (1), (2) or (7) is an inert alkane, and if it has a lower boiling point, it is volatilized out of the system during the reaction, or if it has a high boiling point, it remains in the solution and even if it remains in the system, it is inert to the succeeding reaction.

A byproduct in the processes of (3) to (5) is an alkali metal halide MX (such as lithium chloride, sodium chloride, potassium chloride or the like), and precipitates in an inert hydrocarbon solvent and can be easily removed by filtration. Among the above processes, the processes (1), (2), (6) and (7) are particularly preferable since various trialkylaluminums and dialkylaluminum alkoxides are available and an operation of removing the precipitate formed after the reaction is not necessary.

A catalyst system used for producing an ethylene polymer in accordance with the present invention comprises the above chromium catalyst and an organoaluminum compound of the above formula (1) or formula (102). Preferable examples of the organoaluminum compound include compounds of the above formula (2), (3), (4) or (103), and further a compound of the formula (5). More preferably, compounds illustrated as preferable ones in the explanation of the above formula (101) are usable. An organoaluminum compound expressed by the formula (102) of the present invention is a novel alkylaluminum compound having both an alkoxide group and a siloxide group, and enhances a response to hydrogen of a chromium catalyst and thus a unique property that an amount of α-olefin byproduced is small. The details of this reason are not clear, but it is considered that an alkoxide group and a siloxide group have respectively different functions to chromium.

(Method for Producing Ethylene Polymer)

A method for producing an ethylene polymer of the present invention by using the above chromium catalyst and organoaluminum compound can be carried out by any process of gas phase polymerization or liquid phase polymerization such as slurry polymerization.

The liquid phase polymerization process is usually carried out in a hydrocarbon solvent. As the hydrocarbon solvent, an inert hydrocarbon such as propane, n-butane, isobutane, n-pentane, isopentane, hexane, heptane, octane, decane, cyclohexane, benzene, toluene, or xylene may be used alone or in a mixture. Particularly, a slurry polymerization is preferable since an ethylene polymer is hardly soluble in a solvent and a slurry state can be maintained even when a polymerization temperature is raised for producing a low molecular weight ethylene polymer. Preferable examples of the slurry solvent include hydrocarbons such as propane, n-butane, isobutane or the like.

A gas phase polymerization process may be carried out in the presence of an inert gas by employing a polymerization method using a fluidized bed, a stirring bed or the like, and a medium for removing polymerization heat may be present, i.e. condensing mode may be employed, if necessary.

A polymerization temperature is generally from 60 to 120° C., preferably from 70 to 110° C., more preferably from 80 to 105° C. A catalyst concentration and an ethylene concentration in a reactor may be any optional concentration as far as polymerization proceeds. For example, a catalyst concentration may be in a range of from about 0.0001 to about 5 mass % on the basis of a mass amount of the content in a reactor in a case of slurry polymerization. Also, the ethylene concentration may be in a range of from 0.1 to 10 MPa as the total pressure in a case of gas phase polymerization.

In the multistage polymerization process of the present invention, an organoaluminum compound may be introduced into any stage of a reactor or into all stages of the reactor. For example, when an organoaluminum compound is introduced into the first stage polymerization reactor, an organoaluminum compound which is not consumed in the polymerization reaction is flown into any of the succeeding stages.

Even when an organoaluminum compound is flown as mentioned above, a catalyst function of a chromium catalyst is not reformed by the introduced organoaluminum compound alone and therefore it is possible to carry out polymerization in the same manner as in the case of not introducing an organoaluminum compound.

Accordingly, when an organoaluminum compound is introduced into the first stage, the organoaluminum compound flown from the former stage is present in a polymerization reactor, into which hydrogen is introduced for the purpose of lowering a molecular weight in the latter stage. Thus, an organoaluminum compound may be present from the first stage.

However, a preferable method of introducing an organoaluminum compound is to introduce, together with hydrogen, into the stage of a polymerization reactor wherein a molecular weight should be lowered.

When introducing an organoaluminum compound, it may be introduced as it is or may be introduced together with an inert dispersion medium. It is preferable to introduce an organoaluminum compound as a diluted liquid of an inert hydrocarbon solvent such as n-pentane, isopentane, hexane, heptane, octane, decane, cyclohexane, benzene, toluene, xylene or the like. A diluted liquid may have any optional concentration, but it is preferable to employ a low concentration of at most 15 mass % for safety. An organoaluminum compound in the reactor may also have any optional concentration, but it is preferable to adjust a feeding amount in such a manner as to adjust a mol ratio of an organoaluminum compound and a chromium catalyst in the reactor to an Al/Cr mol ratio of from 0.01 to 100, preferably from 0.1 to 10, more preferably from 0.5 to 5. If this mol ratio is less than 0.01, a chain transfer agent to hydrogen does not substantially work, and if the mol ratio exceeds 100, an activity is largely lowered, such being unpreferable.

In the present invention, it is preferable to introduce an organoaluminum compound as a co-catalyst separately from a chromium catalyst into the polymerization system. In the present invention, an organoaluminum compound of the formula (1) or the formula (102) is introduced into the reaction system together with or separately from a chromium catalyst. Thus, the polymerization by the chromium catalyst is carried out in the presence of an organoaluminum compound of the formula (1) or the formula (102).

The first function of an organoaluminum compound as a co-catalyst is to reform a chromium catalyst hardly causing chain transfer to hydrogen into a chromium catalyst capable for chain transfer to hydrogen. The details of this function are not clear, but it is considered that a part of chromium on the catalyst is converted to an active site for dissociating a hydrogen molecule by the action of the organoaluminum compound and to cause chain transfer by the dissociated hydrogen atom working on a polymerization active site. In this manner, a low molecular weight ethylene polymer is obtained. Also, if the chain transfer to hydrogen is caused, it is possible to narrowing a molecular weight distribution. Thus, it is possible to produce a low molecular weight polymer and to narrow a molecular weight distribution at the same time. If the low molecular weight component has a wide molecular weight distribution, the product thus obtained causes fuming and a gum content is increased, such being unpreferable, but in the present invention, the molecular weight distribution is satisfactorily narrow, and these problems are not substantially caused.

The second function of an organoaluminum compound of the formula (1) or the formula (102) is to reduce an amount of α-olefin byproduced, which is one of important features. In the ethylene polymerization using a chromium catalyst, when an organometallic compound such as a trialkylaluminum is used as a co-catalyst, α-olefin comprising 1-hexene as the main component is easily byproduced, and it is well known that the byproduced α-olefin works as a comonomer to be copolymerized, and consequently lowers a density of an ethylene polymer obtained.

For example, a trialkylaluminum $(R^{101})_3Al$ is often used as a co-catalyst for ethylene polymerization, but it causes byproduction of α-olefin although an amount of α-olefin byproduced varies depending on the polymerization conditions and it lowers a density of an ethylene polymer. Also, an alkylaluminum disiloxide $R^{101}Al(OSiR^{103}R^{104}R^{105})_2$ causes byproduction of α-olefin, and lowers a density of an ethylene polymer obtained. An alkylaluminum dialkoxide $R^{101}Al(OR^{102})_2$, an aluminum trialkoxide $Al(OR^{102})_3$, an aluminum trisiloxide $Al(OSiR^{103}R^{104}R^{105})_3$ or the like may generally belong to an organoaluminum compound, but has such a strong poisoning function to a chromium catalyst as to largely lower a polymerization activity or to terminate the polymerization.

Unlike the above-mentioned organoaluminum compound conventionally used, an organoaluminum compound of the formula (102) used in the present invention hardly byproduces α-olefin even when using in combination with a chromium catalyst. Therefore, a density of a product produced is not lowered, and it is easy to obtain a product having an aimed density.

Also, the third function of an organoaluminum compound of the formula (102) is to remarkably lower copolymerizability of α-olefin. Accordingly, even if α-olefin is byproduced, the byproduced α-olefin is hardly copolymerized, and consequently the lowering of density of an ethylene polymer obtained is hardly caused.

Thus, an organoaluminum compound of the formula (102) of the present invention is a novel alkylaluminum compound having both an alkoxide group and a siloxide group, and improves a response to hydrogen of a chromium catalyst and prevents byproduction of α-olefin, which is a unique property. The details of this reason are not clear, but it is considered that each function of an alkoxide group and a siloxide group to chromium is respectively different.

In the polymerization method of the present invention, hydrogen may be present if required. Hydrogen works as a chain transfer agent for adjusting a molecular weight in the same manner as in the case of polymerization by a Ziegler catalyst or a metallocene catalyst. Since an organoaluminum compound of the above formula is present, a hydrogen response of a chromium catalyst is improved. Therefore, it is possible to use hydrogen for adjusting a molecular weight. Also, it is possible to obtain an ethylene polymer having a relatively high molecular weight by carrying out polymerization without introducing hydrogen.

In the present invention, hydrogen is introduced into an optional stage of a polymerization reactor for the purpose of lowering a molecular weight. In order to lower the molecular weight, it is necessary to introduce an organoaluminum compound at the same time of introducing hydrogen into the hydrogen-introducing stage of a polymerization reactor or to have an organoaluminum compound present at a predetermined density in the same stage of the polymerization reactor into which an organoaluminum compound is flown from other stage. In the method of the present invention, a high molecular weight component is produced at an initial stage, and a low molecular weight component is produced at a latter stage. Accordingly, it is preferable to introduce hydrogen into the second or succeeding stages of the polymerization reactor into which the above organoaluminum compound is introduced or to introduce hydrogen into the polymerization reactor into which the organoaluminum compound is flown.

Here, hydrogen works as a chain transfer agent for adjusting a molecular weight in the same manner as in a case of polymerization by a Ziegler catalyst or by a metallocene catalyst. Since the above-mentioned organoaluminum compound is present, a response to hydrogen of a chromium catalyst is improved, and it is possible to use hydrogen satisfactorily adjusting a molecular weight.

A hydrogen pressure is not specially limited, but a hydrogen concentration in liquid phase in the case of slurry polymerization process is usually from $1.0 \times 10^{-5}$ to $1.0 \times 10^{1}$ mass %, preferably from $5.0 \times 10^{-4}$ to $5.0 \times 10^{-2}$ mass %, and a hydrogen partial pressure in gas phase in the case of gas phase polymerization process is from $1.0 \times 10^{-3}$ to 10.0 MPa, preferably from $5.0 \times 10^{-2}$ to 5.0 MPa. Also, an ethylene concentration in liquid phase in the case of slurry polymerization process is usually from 1.0 to 20.0 mass %, preferably from 2.0 to 15.0 mass %, and an ethylene partial pressure in gas phase in the case of gas phase polymerization process is from 1.0 to 20.0 MPa, preferably from 2.0 to 15.0 MPa.

If it is necessary to adjust a density, it is possible to carry out copolymerization by introducing α-olefin such as propylene, 1-butene, 1-pentene, 1-hexene, 4-methyl-1-pentene, 1-octene or the like respectively alone or in a mixture of two or more into a reactor. Here, an α-olefin content in an ethylene polymer produced in the present invention is preferably at most 15 mol %, more preferably at most 10 mol %. Accordingly, an amount of α-olefin supplied may be adjusted in such a manner as to correspond to the above α-olefin content.

According to the present invention, in order to improve both of ESCR and creep resistance at the same time, a branch is selectively imparted to a high molecular weight component by introducing a comonomer. A preferable method for this purpose is to introduce a comonomer (α-olefin) into the stage of producing a high molecular weight component in the polymerization reactor.

Therefore, it is necessary to introduce a comonomer selectively into a specific stage for producing a high molecular weight component. As described above, it is preferable to produce a high molecular weight component at an initial stage. Thus, the introduction of a comonomer for imparting a branch is carried out at the initial polymerization stage in the reactor, and the comonomer is not positively introduced into the latter stage of the polymerization reactors, but in a continuous production process, an unreacted material of the introduced α-olefin is flown into the latter stage. However, since an amount of the unreacted material to be flown as a comonomer is small, its influence is small. Also, as described above, in the catalyst system of the present invention having an organoaluminum compound introduced therein, an amount of α-olefin byproduced is small, and even if α-olefin is byproduced, copolymerizability of the α-olefin with ethylene is low, or because of both reasons, it is little that α-olefin (comonomer) copolymerizes.

Therefore, according to the method of the present invention, it is possible to selectively employ a method for introducing a comonomer (α-olefin) selectively into an initial stage of multistage polymerization since even if the comonomer is flown into the latter stage, its influence is small.

In the present invention, it is essential to carry out multistage polymerization by connecting at least two reactors in series in order to widen a molecular weight distribution. It is preferable for the multistage polymerization to employ a multistage polymerization process which comprises connecting at least two reactors in series and supplying a reaction mixture obtained by polymerization in the first stage reactor to a second stage or succeeding reactors.

Hereinafter, the multistage polymerization process of the present invention is explained by taking the case of two stage polymerization as an example. When carrying out multistage continuous polymerization in series, a chromium catalyst added to the first stage is flown into the second stage of the reaction system. Also, the chromium catalyst may be optionally added to the second stage if necessary.

A polymerization reaction mixture is transferred from the first stage reactor to the second stage reactor by a pressure difference through a connecting conduit and by continuously discharging the polymerization reaction mixture from the second stage reactor.

It is preferable that a specific molecular weight component is produced in each stage. For example, it is preferable that a high molecular weight component is produced in the first stage reactor and a low molecular weight component is produced in the second stage reactor, but it is possible to produce a low molecular weight component in the first stage reactor and to produce a high molecular weight component in the second stage reactor.

Since the catalyst system of the present invention has a good response to hydrogen, it is possible to use hydrogen for adjusting a molecular weight. When using hydrogen for adjusting a molecular weight, it is preferable for productivity to employ a system wherein a high molecular weight component is produced in the first stage reactor and a low molecular weight component is produced in the second stage reactor since a hydrogen flush tank is not required in an intermediate step in such a case.

That is, it is economically favorable in view of an equipment cost to introduce hydrogen into the second stage polymerization reactor without introducing hydrogen into the first stage polymerization reactor, thus omitting a hydrogen flush tank in the intermediate step.

It is necessary to have an organoaluminum compound present in the second stage polymerization reactor into which hydrogen is introduced.

The organoaluminum compound may be introduced into the stage of the polymerization reactor into which hydrogen is introduced, or may be introduced into the first stage and then flown into the second stage consequently to have the organoaluminum compound present in the second stage. Also, it is possible to introduce the same or different organoaluminum compounds respectively into the first stage and the second stage.

In the first stage, polymerization of ethylene alone, or ethylene and α-olefin added as required, is carried out. When introducing hydrogen, a polymerization reaction is carried out by controlling a mass amount ratio or a partial pressure ratio of a hydrogen concentration to an ethylene concentration, a polymerization temperature or both factors to adjust a molecular weight, or by controlling a mass ratio or a partial pressure ratio of an α-olefin concentration to an ethylene concentration to adjust a density.

In the second stage, hydrogen in the reaction mixture flown from the first stage and α-olefin flown from the first stage are present, but fresh hydrogen or α-olefin may be added if necessary.

Accordingly, in the second stage also, the polymerization reaction is carried out by controlling a mass amount ratio or a partial pressure ratio of a hydrogen concentration to an ethylene concentration, a polymerization temperature or both factors to adjust a molecular weight, or by controlling a mass amount ratio or a partial pressure ratio of an α-olefin concentration to an ethylene concentration to adjust a density.

In order to improve both ESCR and creep resistance at the same time, the method of the present invention copolymerizes ethylene by introducing α-olefin to lower a density. Preferably, in order to impart a branch selectively to a high molecular weight component for lowering a density, α-olefin as a comonomer is introduced into the high molecular weight component-producing stage of a polymerization reactor. According to the method of the present invention, it is possible to introduce α-olefin into both of the first stage and the second stage, but α-olefin must be introduced into at least the first stage since the high molecular weight component is produced at the initial stage. Unreacted material of the comonomer introduced into the first stage is flown into the second stage and succeeding stages of the polymerization reactor, but its amount is small and the flown comonomer does not adversely affect on the latter stage.

When using a specific organoaluminum compound of the present invention, monostage polymerization for producing an ethylene polymer by using one reactor is employed, or multistage polymerization having at least two reactors connected in series is preferably employed for widening a molecular weight distribution. In the case of multistage polymerization, it is preferable to employ multistage polymerization having at least two reactors connected in series, wherein a reaction mixture obtained by polymerization in the first stage reactor is continuously supplied to the second stage reactor.

As already mentioned above, the organoaluminum compound of the present invention has functions of reducing byproduction of α-olefin and preventing lowering of a density. If a density of a low molecular weight component obtained in the second stage is lowered, a short chain branch contained in a high molecular weight component in a finally obtained ethylene polymer is relatively reduced in the same density, and consequently ESCR or creep resistance is degraded.

In the production by two stage polymerization, a ratio of a high molecular weight component and a low molecular weight component is from 10 to 90 mass parts of a high molecular weight component and from 90 to 10 mass parts of a low molecular weight component, preferably from 20 to 80 mass parts of a high molecular weight component and from 80 to 20 mass parts of a low molecular weight component, more preferably from 30 to 70 mass parts of a high molecular weight component and from 70 to 30 mass parts of a low molecular weight component. Also, a high molecular weight component has an HLMFR of from 0.01 to 100 g/10 minutes, preferably from 0.01 to 50 g/10 minutes, and a low molecular weight component has an HLMFR of from 0.1 to 1,000 g/10 minutes, preferably from 0.1 to 500 g/10 minutes.

As mentioned above, a polymerized material formed in the first stage is withdrawn from the first stage polymerization reactor, and a reaction mixture containing an unreacted material is transferred to the second stage.

The reaction mixture withdrawn from the final stage reactor is formed into a product optionally by removing a solvent and drying in the case of slurry polymerization. Well known additives may be optionally added at the time of forming a product or thereafter.

(Ethylene Polymer)

It is preferable to knead the ethylene polymer thus obtained optionally in accordance with a well known method. The kneading can be carried out by a monoaxial or biaxial extruder or a continuous system kneader. Also, the ethylene polymer thus obtained can be molded by a usual molding method such as blow-molding or extrusion-molding.

For example, according to the method of the present invention, an ethylene polymer having an HLMFR of from 1 to 100 g/10 minutes, preferably from 2 to 80 g/10 minutes, a density of from 0.930 to 0.970 g/cm$^3$, preferably from 0.935 to 0.965 g/cm$^3$, can be obtained. Particularly, the ethylene polymer obtained by the multistage polymerization of the present invention provides a wider molecular weight distribution and contains a high molecular weight component having a short chain branch introduced in a larger amount, thus providing high ESCR or creep resistance, as compared with a polymer obtained by using a general chromium catalyst.

In the case of using a general chromium type catalyst, a molecular weight distribution has an Mw/Mn value of usually from 10 to 15 measured by GPC. On the other hand, according to the method of the present invention, a molecular weight distribution curve obtained by GPC measurement is not such a degree as exhibiting bimodal but has an Mw/Mn value of from 16 to 25 by GPC measurement. Thus, as compared with a resin obtained by a conventional chromium type catalyst without introducing an organoaluminum compound of the present invention or preferably a resin obtained in the first stage, a resin obtained in the second stage in accordance with the method of the present invention widens a molecular weight distribution (Mw/Mn value). For example, it is possible to widen a molecular weight distribution (Mw/Mn value) by at least 5%, preferably at least 10%, more preferably at least 20% in the present invention.

Therefore, a more satisfactory effect can be achieved in respect of articles molded by a blow-molding method or an extrusion-molding method. A polymer for blow-molding has an HLMFR value of from 1 to 100 g/10 minutes and a density of from 0.935 to 0.965 g/cm$^3$. Particularly, an ethylene polymer for small type blow-molded articles has an HLMFR value of from 20 to 50 g/10 minutes and a density of from 0.940 to 0.965 g/cm$^3$, and an ethylene polymer for large type blow-molded articles has an HLMFR value of from 2 to 10 g/10 minutes and a density of from 0.940 to 0.965 g/cm$^3$. An ethylene polymer for extrusion-molded articles has an HLMFR value of from 10 to 30 g/10 minutes and a density of from 0.935 to 0.950 g/cm$^3$.

EXAMPLES

Hereinafter, the present invention is further illustrated with reference to Examples and Comparative Examples, but should not be limited to the Examples. The measuring methods employed in the Examples and Comparative Examples are illustrated below.

a) Pretreatment of Polymer for Measuring Physical Properties:

Polymer was kneaded at 190° C. for 7 minutes in a nitrogen atmosphere by using plastograph (Laboplastomill ME25; R608 type roller shape) manufactured by TOYO SEIKI KOGYO CO,. LTD. and adding 0.2 mass % of IRGANOX B225, manufactured by Ciba Geigy Company as an additive.

b) Melt Flow Rate (HLMFR):

HLMFR was measured at a temperature of 190° C. under a load of 211.82 N in accordance with Table 1, condition 7 of JIS K-7210 (1996).

c) Density:

Density was measured in accordance with JIS K-7112 (1996).

d) Molecular Weight Distribution (Mw/Mn):

An ethylene polymer produced was subjected to gel permeation chromatography (GPC) under the following conditions to measure a number average molecular weight (Mn) and a weight average molecular weight (Mw) and to calculate a molecular weight distribution (Mw/Mn).

(GPC Measuring Conditions)

Apparatus: WATERS 150 C Model, Column: Shodex-HT806M, Solvent: 1,2,4-trichlorobenzene, Temperature: 135° C., Universal evaluation by using monodispersed polystyrene fraction.

With regard to a molecular weight distribution (the larger Mw/Mn, the wider molecular weight distribution) expressed by a ratio (Mw/Mn) of Mw to Mn, a molecular weight disclosed in "Size exclusion chromatography (high performance liquid chromatography)" (written by Sadao Mori, published by Kyoritsu Shuppan, p. 96) and n-alkane and fractional straight chain polyethylene data of Mw/Mn≦1.2 were applied to the formula of a detector sensitivity to determine a sensitivity of molecular weight M expressed by the following formula and to compensate a measured value of a sample.

Sensitivity of molecular weight M=a+b/M (a and b are fixed numbers, a=1.032, b=189.2)

e) Environmental Stress Cracking Resistance (ESCR):

F50 value of BTL (Bell Telephone Laboratory) method measured in accordance with JIS K-6760 (1996) was determined to be ESCR (hr) value.

f) Creep Resistance:

Whole circumference notch type tensile creep measurement (short test) was carried out in accordance with JIS K-6774 (1996) to measure a breakage time at a stress of 6 MPa which is determined to be a creep resistance value.

Example 1

Into a first stage reactor having an internal volume of 150 L, were continuously charged 50 L/hr of isobutane, 5 g/hr of HA30 catalyst (chromium atom carried amount=1.0 mass %) manufactured by Grace Company (previously activated by calcination at 750° C. for 8 hours), 12 kg/hr of ethylene and 0.8 L/hr of 1-hexene, and first stage polymerization was continuously carried out in a liquid-filled state under conditions of 85° C., a total pressure of 4.1 MPa and an average residence time of 1.0 hr by discharging the reactor content at a predetermined rate. An isobutane slurry containing a polymer produced in the first stage reactor was continuously withdrawn, and was introduced through a connecting tube having an inner diameter of 50 mm into a second stage reactor having an internal volume of 300 L. At this time, a part of the polymer was taken out of the system. The polymer thus taken out of the system had an HLMFR value of 1.0 g/10 minutes and a density of 0.9365 g/cm$^3$. Into the second stage reactor, were continuously charged 2.4 g/hr (Al/Cr mol ratio=2) of a 15 mass % hexane solution of diethylaluminum ethoxide manufactured by Tosoh•Finechem K.K. and 15 g/hr of hydrogen at 85° C., without adding a catalyst, and second stage polymerization was carried out under conditions of a total pressure of 4.1 MPa and an average residence time of 1.0 hr to obtain polyethylene. A high molecular weight component ratio in the first stage was 50 mass parts, and a low molecular weight component ratio in the second stage was 50 mass parts. The polyethylene thus obtained had an ESCR value of 420 hr and a breakage time of 70 hr. Other measurement results of physical properties are shown in Table 1. Thus, an ethylene polymer excellent in ESCR and creep resistance could be obtained.

Comparative Example 1

Into a first stage reactor having an internal volume of 150 L, were continuously charged 50 L/hr of isobutane, 5 g/hr of HA30 catalyst (chromium atom carried amount=1.0 mass %) manufactured by Grace Company (previously activated by calcination at 750° C. for 8 hours), 12 kg/hr of ethylene and 0.6 L/hr of 1-hexene, and first stage polymerization was continuously carried out in a liquid-filled state under conditions of 90° C., a total pressure of 4.1 MPa and an average residence time of 1.0 hr by discharging the reactor content at a predetermined rate. An isobutane slurry containing a polymer produced in the first stage reactor was continuously withdrawn, and was introduced through a connecting tube having an inner diameter of 50 mm into a second stage reactor having an internal volume of 300 L. At this time, a part of the polymer was taken out of the system. The polymer thus taken out of the system had an HLMFR value of 2.6 g/10 minutes and a density of 0.9395 g/cm$^3$. Into the second stage reactor, was continuously charged 15 g/hr of hydrogen at 103° C., without adding a catalyst, and second stage polymerization was carried out under conditions of a total pressure of 4.1 MPa and an average residence time of 1.0 hr to obtain polyethylene. A high molecular weight component ratio in the first stage was 50 mass parts, and a low molecular weight component ratio in the second stage was 50 mass parts. The polyethylene thus obtained had an ESCR value of 240 hr and a breakage time of 50 hr. Other measurement results of physical properties are shown in Table 1. The ethylene polymer thus obtained was poor in ESCR and creep resistance as compared with those of Example 1.

Both of the resins of Example 1 and Comparative Example 1 are resins for large type blow-molded products, and reaction conditions were determined in such a manner as to provide an HLMFR value (second stage in total) in the vicinity of 6 g/10 minutes in view of molding processibility.

Phillips catalysts of Comparative Example 1 and Example 1 provide a resin having a considerably higher molecular weight at a usual reaction temperature. Thus, in Example 1, molecular weight adjustment was carried out with hydrogen by introducing an organoaluminum compound and a polymerization temperature was maintained low, and in Comparative Example 1, since an organoaluminum compound was not introduced and hydrogen introduced into the second stage reactor did not have a substantial effect for lowering a molecular weight, the molecular weight was lowered by raising a polymerization temperature.

With regard to a density, 1-hexene was introduced into the first stage in both Example 1 and Comparative Example 1, and it was aimed to obtain products having almost the same density.

As evident from the density results in Table 1, a larger amount of 1-hexene was required in Example 1 in order to aim at obtaining the same density in the final product although there may be a difference in catalyst efficiency. The fact of requiring a larger amount of 1-hexene in Example 1 to obtain the same density means that 1-hexene is flown from the first stage although 1-hexene is not introduced into the second stage, and copolymerization of 1-hexene occurs in the second stage, but the organoaluminum compound of Example 1 has an effect of lowering copolymerizability of α-olefin to ethylene. In other words, it is meant that in the case of producing an ethylene polymer having the same HLMFR and the same density, an amount of a comonomer introduced for a low molecular weight component can be small and a larger amount of a comonomer for a high molecular weight component can be introduced in Example 1 as compared with Comparative Example 1. This is important in respect of ESCR and creep resistance.

TABLE 1

| Example No. | Organoaluminum compound | Polymerization temperature (° C.) | Hydrogen partial pressure (MPa) | 1-hexene (g) |
| --- | --- | --- | --- | --- |
| 1 | Et$_2$Al (OEt) | First stage: 85° C. Second stage: 85° C. | First stage: not introduced Second stage: 15 g/hr | First stage: 0.8 L/hr Second stage: not introduced |
| Comp. Ex. 1 | — | First stage: 90° C. Second stage: 103° C. | First stage: not introduced Second stage: 15 g/hr | First stage: 0.6 L/hr Second stage: not introduced |

TABLE 1-continued

| Example No. | HLMFR (g/10 min) | Density (g/cm³) | Mn (×10⁴) | Mw (×10⁴) | Mw/Mn |
|---|---|---|---|---|---|
| 1 | First stage: 1.0 Second stage in total: 5.8 | First stage: 0.9365 Second stage in total: 0.9445 | 1.8 | 37.7 | 20.9 |
| Comp. Ex. 1 | First stage: 2.6 Second stage in total: 6.0 | First stage: 0.9395 Second stage in total: 0.9446 | 2.5 | 36.0 | 14.4 |

Example 2

(1) Preparation of ethylaluminum(ethoxide)(trimethyl siloxide) (EtAl(OEt)(OSiMe$_3$))

0.77 mL (5 mmol) of diethylaluminum ethoxide manufactured by Tosoh•Finechem K.K. and 30 mL of dehydration-purified hexane were charged into a two-necked flask of 100 mL equipped with a refluxing cooler and flushed with nitrogen, and were dissolved.

After cooling at 0 to 5° C. in an ice bath, 0.56 mL (5 mmol) of trimethylsilanol manufactured by Shin-Etsu Chemical Co., Ltd. was added dropwise thereto for about 2 minutes. The ice bath was replaced by an oil bath, and the content was heated at an outer temperature of 80° C. for 2 hours by refluxing with hexane. Thus, 0.16 mol/L-hexane solution of ethylaluminum(ethoxide)(trimethyl siloxide) was obtained. The hexane in this hexane solution was removed under reduced pressure and was dissolved in toluene-d8 and subjected to $^1$H-NMR measurement by GSX-400 manufactured by JEOL Ltd., and its analytical data were CH$_3$CAl(δ 0.83, triplet, 3H), CCH$_2$Al (δ 0.10, quartet, 2H), CH$_3$CO (δ 1.25, triplet, 3H), CCH$_2$O (δ 4.50, quartet, 2H), and CH$_3$SiO (δ 0.27, singlet, 9H).

(2) Polymerization

Into an autoclave of 1.5 L fully flushed with nitrogen, were charged 100 mg of C-34300MS catalyst (chromium atom carried amount=1.0 mass %) of PQ Company, previously activated by calcination in air at 820° C. for 6 hours and 700 mL of isobutane, and an internal temperature was raised to 95° C. Ethylene at a partial pressure of 1.4 MPa was introduced therein, and when the consumption of ethylene was initiated, 0.24 mL of 0.16 mol/L-hexane solution of ethylaluminum(ethoxide)(trimethyl siloxide) (Al/Cr mol ratio=2) prepared in the above paragraph (1) was charged under pressure with nitrogen. While maintaining the ethylene partial pressure at 1.4 MPa, polymerization was carried out at 95° C. for 1 hour. Thereafter, by releasing the inner gas out of the system, the polymerization was terminated. As this result, 230 g of polyethylene was obtained. Polymerization activity per 1 g of catalyst and 1 hour of polymerization time was 2,300 g/g·hr. The measurement results of physical properties (HLMFR, density, molecular weight (Mn, Mw), molecular weight distribution (Mw/Mn)) are shown in Table 2.

Example 3

Polymerization was carried out in the same manner as in Example 1, except that hydrogen was introduced at a partial pressure of 0.2 MPa before introducing ethylene in the step (2) of Example 2. As this result, 240 g of polyethylene was obtained. Polymerization activity per 1 g of catalyst and 1 hour of polymerization time was 2,400 g/g·hr. The measurement results of physical properties are shown in Table 2.

Example 4

Polymerization was carried out in the same manner as in Example 1, except that hydrogen was introduced at a partial pressure of 0.2 MPa before introducing ethylene and 4 g of 1-hexene was introduced together with ethylaluminum (ethoxide)(trimethyl siloxide) in the step (2) of Example 2. As this result, 220 g of polyethylene was obtained. Polymerization activity per 1 g of catalyst and 1 hour of polymerization time was 2,200 g/g·hr. The measurement results of physical properties are shown in Table 2.

Example 5

Two stage polymerization was carried out in the following manner.

Into a first stage reactor having a internal volume of 150 L, were continuously supplied 50 L/hr of isobutane, 5 g/hr of C-34300MS catalyst (chromium atom supported amount=1.0 mass %) of PQ Company (which was previously activated by calcination in air at 820° C. for 6 hours), 12 kg/hr of ethylene and 0.8 L/hr of 1-hexene, and the reactor content was discharged at a predetermined rate, and first stage polymerization was continuously carried out at a state filled with liquid under conditions of 85° C., a total pressure of 4.1 MPa and an average residence time of 1.0 hr. A slurry of isobutane containing the polymer formed in the first stage reactor was continuously withdrawn, and was introduced into a second stage reactor having an internal volume of 300 L through a connecting tube having an inside diameter of 50 mm. At this time, a part of the polymer was taken out of the system. The taken out polymer had an HLMFR of 1.5 g/10 minutes and a density of 0.9302 g/cm³. Into the second stage reactor, were continuously supplied 2.4 g/hr (Al/Cr mol ratio=2) of a 15 mass % hexane solution of ethylaluminum(ethoxide)(trimethyl siloxide) prepared in the step (1) of Example 2 and 15 g/hr of hydrogen, and second stage polymerization was carried out under conditions of a total pressure of 4.1 MPa and an average residence time of 1.0 hr to obtain polyethylene. A ratio of the first stage high molecular weight component was 50 mass parts, and a ratio of the second stage low molecular weight component was 50 mass parts. The polyethylene thus obtained had an ESCR value of 450 hr and a breakage time of 80 hr. Other measurement results of physical properties are shown in Table 2. Thus, an ethylene polymer excellent in ESCR and creep resistance was obtained.

Comparative Example 2

Polymerization was carried out in the same manner as in Example 2, except that ethylaluminum(ethoxide)(trimethyl siloxide) was not introduced in the step (2) of Example 2. As this result, 206 g of polyethylene was obtained. Polymerization activity per catalyst 1 g and polymerization time 1 hour was 2,060 g/g·hr. The measurement results of physical properties are shown in Table 2.

Comparative Example 3

Polymerization was carried out in the same manner as in Example 2, except that hydrogen was introduced at a partial pressure of 0.2 MPa before introducing ethylene and ethylaluminum(ethoxide)(trimethyl siloxide) was not introduced in the step (2) of Example 2. As this result, 191 g of polyethylene was obtained. Polymerization activity per catalyst 1 g and polymerization time 1 hour was 1,910 g/g·hr. The measurement results of physical properties are shown in Table 2. As compared with Example 3 introducing ethylaluminum(ethoxide)(trimethyl siloxide), an HLMFR value did not largely increase, and a molecular weight was not largely lowered.

Comparative Example 4

Polymerization was carried out in the same manner as in Example 2, except that hydrogen was introduced at a partial pressure of 0.2 MPa before introducing ethylene, 4 g of 1-hexene was charged under pressure by nitrogen at the time of initiating consumption of ethylene, and ethylaluminum (ethoxide)(trimethyl siloxide) was not introduced in the step (2) of Example 2. As this result, 180 g of polyethylene was obtained. Polymerization activity per catalyst 1 g and polymerization time 1 hour was 1,800 g/g·hr. The measurement results of physical properties are shown in Table 2. As compared with Example 4 introducing ethylaluminum (ethoxide)(trimethyl siloxide), a density was largely lowered and it was proved that copolymerization occurred.

Comparative Example 5

(1) Preparation of ethylaluminum diethoxide(EtAl(OEt)$_2$)

0.77 mL (5 mmol) of diethylaluminum ethoxide manufactured by Tosoh•Finechem K.K. and 30 mL of dehydration-purified hexane were charged into a two-necked flask of 100 ml equipped with a refluxing cooler and flushed with nitrogen, and were dissolved.

After cooling at 0 to 5° C. in an ice bath, 0.25 mL (5 mmol) of ethanol manufactured by Wako Pure Chemical Industries, Ltd. was added dropwise thereto for about 2 minutes. The ice bath was replaced by an oil bath, and the content was heated at an outer temperature of 80° C. for 2 hours by refluxing with hexane. Thus, 0.16 mol/L-hexane solution of ethylaluminum diethoxide was obtained.

(2) Polymerization

Polymerization was carried out in the same manner as in Example 2, except that 0.24 mL (Al/Cr mol ratio=2) of a 0.16 mol/L-hexane solution of ethylaluminum diethoxide obtained in the above step (1) was used in place of ethylaluminum(ethoxide)(trimethyl siloxide) in Example 2 (2). As this result, 15 g of polyethylene was obtained. Polymerization activity per 1 g of catalyst and 1 hour of polymerization time was 150 g/g·hr. Since the activity was remarkably lowered and a polyethylene yield was very low, evaluation of physical properties was not carried out.

Comparative Example 6

(1) Preparation of ethylaluminum di(trimethyl siloxide) (EtAl(OSiMe$_3$)$_2$)

0.68 mL (5 mmol) of triethylaluminum manufactured by Tosoh•Finechem K.K. and 30 mL of dehydration-purified hexane were charged into a two-necked flask of 100 ml equipped with a refluxing cooler and flushed with nitrogen, and were dissolved.

After cooling at 0 to 5° C. in an ice bath, 1.11 mL (10 mmol) of trimethylsilanol manufactured by Shin-Etsu Chemical Co., Ltd. was added dropwise thereto for about 2 minutes. The ice bath was replaced by an oil bath, and the content was heated at an outer temperature of 80° C. for 2 hours by refluxing with hexane. Thus, 0.16 mol/L-hexane solution of ethylaluminum di(trimethyl siloxide) was obtained.

(2) Polymerization

Polymerization was carried out in the same manner as in Example 2, except that 0.24 mL (Al/Cr mol ratio=2) of a 0.16 mol/L-hexane solution of ethylaluminum di(trimethyl siloxide) obtained in the above step (1) was used in place of ethylaluminum(ethoxide)(trimethyl siloxide) in Example 2 (2). As this result, 161 g of polyethylene was obtained. Polymerization activity per 1 g of catalyst and 1 hour of polymerization time was 1,610 g/g·hr. As compared with Comparative Example 2, an HLMFR value was raised and a molecular weight was lowered, but a density was largely lowered. The reason why the density was lowered in spite of ethylene homopolymerization, was that α-olefin was byproduced and this was copolymerized. Actually, when measuring $^{13}$C-NMR of the polyethylene thus obtained, it was observed that an ethyl branch derived from 1-butene was 0.7 piece per 1,000 carbon atoms and a butyl branch derived from 1-hexene was 3.4 pieces per 1,000 carbon atoms.

Comparative Example 7

Two Stage Polymerization

Into a first stage reactor having an internal volume of 150 L, were continuously supplied 50 L/hr of isobutane, 5 g/hr of C-34300MS catalyst (chromium atom supported amount=1.0 mass %) of PQ Company (which was previously activated by calcination in air at 820° C. for 6 hours), 12 kg/hr of ethylene and 0.6 L/hr of 1-hexene, and the reactor content was discharged at a predetermined rate, and first stage polymerization was continuously carried out at a stage filled with liquid under conditions of 90° C., a total pressure of 4.1 MPa and an average residence time of 1.0 hr. A slurry of isobutane containing the polymer formed in the first stage reactor was continuously withdrawn, and was introduced into a second stage reactor having an internal volume of 300 L through a connecting tube having an inside diameter of 50 mm. At this time, a part of the polymer was taken out of the system. The taken out polymer had an HLMFR of 3.2 g/10 minutes and a density of 0.9330 g/cm$^3$. Into the second stage reactor, was continuously supplied 15 g/hr of hydrogen, without adding a catalyst, and second stage polymerization was carried out under conditions of a total pressure of 4.1 MPa and an average residence time of 1.0 hr to obtain polyethylene. A ratio of the first stage high molecular weight component was 50 mass parts, and a ratio of the second stage low molecular weight component was 50 mass parts. The polyethylene thus obtained had an ESCR value of 260 hr and a breakage time of 55 hr. Other measurement results of physical properties are shown in Table 2. The ethylene polymer thus obtained was poor in ESCR and creep resistance as compared with those of Example 5.

TABLE 2

| Example No. | Organoaluminum compound | Polymerization temperature (° C.) | Hydrogen partial pressure (MPa) | 1-hexene (g) |
|---|---|---|---|---|
| 2 | EtAl (OEt) (OSiMe$_3$) | 95 | 0 | 0 |
| 3 | EtAl (OEt) (OSiMe$_3$) | 95 | 0.2 | 0 |
| 4 | EtAl (OEt) (OSiMe$_3$) | 95 | 0.2 | 4 |
| 5 (Two stage polymerization) | EtAl (OEt) (OSiMe$_3$) | First stage: 85° C. Second stage: 85° C. | First stage: not introduced Second stage: 15 g/hr | First stage: 0.8 L/hr Second stage: not introduced |
| Comp. Ex. 2 | — | 95 | 0 | 0 |
| Comp. Ex. 3 | — | 95 | 0.2 | 0 |
| Comp. Ex. 4 | — | 95 | 0.2 | 4 |
| Comp. Ex. 5 | EtAl (OEt)$_2$ | 95 | 0 | 0 |
| Comp. Ex. 6 | EtAl (OSiMe$_3$)$_2$ | 95 | 0 | 0 |
| Comp. Ex. 7 (Two stage polymerization) | — | First stage: 90° C. Second stage: 103° C. | First stage: not introduced Second stage: 15 g/hr | First stage: 0.6 L/hr Second stage: not introduced |

| Example No. | Polymerization activity (g/g · hr) | HLMFR (g/10 min) | Density (g/cm$^3$) | Mn (×10$^4$) | Mw (×10$^4$) | Mw/Mn |
|---|---|---|---|---|---|---|
| 2 | 2300 | 4.8 | 0.9555 | 3.0 | 32.5 | 10.8 |
| 3 | 2400 | 45.0 | 0.9590 | 1.6 | 12.8 | 8.0 |
| 4 | 2200 | 52.5 | 0.9551 | 1.3 | 10.3 | 7.9 |
| 5 (Two stage polymerization) | — | First stage: 1.5 Second stage in total: 6.0 | First stage: 0.9302 Second stage in total: 0.9442 | 1.8 | 34.4 | 19.1 |
| Comp. Ex. 2 | 2060 | 3.4 | 0.9553 | 2.9 | 35.3 | 12.2 |
| Comp. Ex. 3 | 1910 | 4.2 | 0.9557 | 3.2 | 33.1 | 10.3 |
| Comp. Ex. 4 | 1800 | 7.4 | 0.9412 | 2.0 | 26.8 | 13.4 |
| Comp. Ex. 5 | 150 | — | — | — | — | — |
| Comp. Ex. 6 | 1610 | 5.8 | 0.9492 | 2.2 | 29.3 | 13.3 |
| Comp. Ex. 7 (Two stage polymerization) | — | First stage: 3.2 Second stage in total: 6.2 | First stage: 0.9330 Second stage in total: 0.9440 | 2.5 | 35.0 | 14.0 |

According to the multistage polymerization method of the present invention which comprises introducing a comonomer into a first stage for preparing a high molecular weight component and introducing a specific organoaluminum compound and hydrogen into a latter stage for preparing a low molecular weight component when polymerizing ethylene by multistage polymerization using a catalyst employing a Phillips catalyst as a base, it is possible to obtain an ethylene-based resin having both of ESCR and creep resistance properties improved and having a wide molecular weight distribution while securing a certain satisfactory molding processibility in spite of a high molecular weight.

Also, according to the present invention employing a specific organoaluminum compound for producing an ethylene polymer by using a chromium catalyst, hydrogen works as a chain transfer agent and copolymerizability is remarkably lowered. By using this organoaluminum in at least a final stage polymerization reactor of multistage polymerization, a molecular weight distribution can be widened, and a short chain branch can be predominantly introduced into a high molecular weight component. As this result, an ethylene copolymer excellent in ESCR and creep resistance properties can be obtained.

What is claimed is:

1. A method for producing an ethylene polymer, which comprises:
   continuously copolymerizing ethylene and a C$_3$-C$_8$ α-olefin in a plurality of reaction zones connected in series in the presence of a chromium catalyst having at least a part of the chromium atoms converted to hexavalent chromium supported on an inorganic oxide support by calcination-activating in a non-reducing atmosphere and which comprises the following steps (1) to (4):
   (1) copolymerizing ethylene and the α-olefin in a slurry state by introducing the chromium catalyst, ethylene, the α-olefin and a reaction solvent into the first reaction zone,
   (2) withdrawing a part or all of a reaction mixture including the catalyst and the reaction medium from the reaction zone and transferring the withdrawn portion to a next reaction zone,
   (3) continuing the slurry polymerization by introducing hydrogen, an organoaluminum compound having the formula (2), $$R^6R^7Al(OCR^8R^9R^{10}) \quad (2)$$

wherein in the above formula, R$^6$ and R$^7$ may be the same or different, and each represents a C$_1$-C$_{18}$ alkyl group; R$^8$, R$^9$ and R$^{10}$ may be the same or different, and each represents a hydrogen atom, a C$_1$-C$_{17}$ alkyl group or a C$_6$-C$_{17}$ aryl group, provided that the total carbon number of R$^8$, R$^9$ and R$^{10}$ is at most 17, as a co-catalyst separately from a chromium catalyst, and ethylene into the reaction zone, to which the reaction mixture is transferred, and
   (4) withdrawing the reaction mixture from the reaction zone to obtain an ethylene polymer.

2. The method for producing an ethylene polymer according to claim 1, wherein an organoaluminum compound having the formula (2) is expressed by the following formula (5),

  (5)

wherein in the above formula, $R^{23}$ and $R^{24}$ may be the same or different, and each represents a $C_1$-$C_{18}$ alkyl group, $R^{25}$ and $R^{26}$ may be the same or different, and each represents a hydrogen atom or a $C_1$-$C_{17}$ alkyl group, provided that the total carbon number of $R^{25}R^{26}$ is at most 17.

3. A method for producing an ethylene polymer according to claim 1, wherein an ethylene polymer has an HLMFR value ranging from 1 to 100 g/10 minutes and a density ranging from 0.930 to 0.970 g/cm$^3$ is obtained.

* * * * *